US006844159B2

(12) United States Patent  (10) Patent No.: US 6,844,159 B2
Tuggle et al.  (45) Date of Patent: Jan. 18, 2005

(54) GENETIC MARKERS FOR SCREENING ANIMALS FOR IMPROVED DISEASE RESISTANCE (NRAMP)

(75) Inventors: Christopher K. Tuggle, Ames, IA (US); Lena Marklund, Ames, IA (US); Thomas J. Stabel, Ames, IA (US); Martha A. Mellencamp, St. Joseph, MO (US); Amber Stumbaugh, San Carlos, CA (US)

(73) Assignees: Iowa State University Research Foundation, Inc., Ames, IA (US); Pig Inprovement Company UK Limited (GB); The United States of America as represented by the Secretary of Agriculture, Washington, DC (US)

( * ) Notice: Subject to any disclaimer, the term of this patent is extended or adjusted under 35 U.S.C. 154(b) by 7 days.

(21) Appl. No.: 10/160,948

(22) Filed: May 31, 2002

(65) Prior Publication Data

US 2003/0129609 A1 Jul. 10, 2003

Related U.S. Application Data

(60) Provisional application No. 60/294,757, filed on May 31, 2001.

(51) Int. Cl.[7] .......................... C12Q 1/68; C12P 19/34; G01N 33/00; C07H 21/02
(52) U.S. Cl. .............................. 435/6; 435/6; 435/91.1; 435/91.2; 435/183; 536/23.1; 536/24.3; 536/24.31; 536/24.33; 536/23.5; 204/456; 436/94
(58) Field of Search .......................... 436/6, 91.1, 91.2, 436/183, 94; 536/23.1, 24.3, 24.31, 24.33, 23.5; 204/456

(56) References Cited

U.S. PATENT DOCUMENTS

| 5,200,313 A | * | 4/1993 | Carrico .......................... 435/6 |
| 6,114,118 A | | 9/2000 | Templeton et al. |
| 6,184,031 B1 | | 2/2001 | Gros et al. |
| 2002/0119455 A1 | * | 8/2002 | Chan ............................. 435/6 |

FOREIGN PATENT DOCUMENTS

| WO | WO 95/13371 | 5/1995 |
| WO | WO 95/2004 | 7/1995 |
| WO | WO 98/12353 | 3/1998 |

OTHER PUBLICATIONS

Zhang et al., Bioinformatics, vol. 19, No. 1, 2003, pp. 14–21.*
Graham et al. Identification of novel alleles at a polymorphic microsatellite repeat region in the human NRAMP1 gene promoter: analysis of allele frequencies in primary biliary cirrhosis. *Journal of Medical Genetics*. 2000:37 pp. 150–152.
Blackwell, Genetics and genomics in infectious disease susceptibility. *Trends in Molecular Medicine*. Nov. 2001:7(11) pp. 521–526.
Moisan et al. Clearance of Infection with Mycobacterium bovis BCG in Mice Is Enhanced by Treatment with S28463 (R–848), and Its Efficiency Depends on Expression of Wild–Type Nramp1 (Resistance Allele). *Antimicrobial Agents and Chemotherapy*, Nov. 2001:45(11) pp. 3059–3064.
Singal et al. NRAMP1 gene polymorphisms in patients with rheumatoid arthritis. *Tissue Antigens*, Jan. 2000:55 pp. 44–47.
Tuggle, et al., Rapid Communication: Cloning of a Pig Full–Length Natural Resistance Associated Macrophage Protein (NRAMP1) cDNA, *J. Anlm. Sci.* 1997, 75:277.
Sun, et al., Mapping of the natural resistance–associated macrophage protein 1 (NRAMP1) gene to pig chromosome 15, International Society for Animal Genetics, *Animal Genetics*, 1998, 29, 138–140.
Zhang, et al, Cloning of Porcine *NRAMP1* and its Induction by Lipopolysaccharide, Tumor Necrosis Factor Alpha, and Interleukin–1 Beta: Role of CD14 and Mitogen–Activated Protein Kinases, *Infection and Immunity*, Mar. 2000, p. 1086–1093.

* cited by examiner

*Primary Examiner*—Bradley L. Sisson
(74) *Attorney, Agent, or Firm*—McKee, Voorhees & Sease, P.L.C.

(57) ABSTRACT

A method for determining improved innate immunity, disease resistance or performance in animals is disclosed. The method involves assays for a genetic differences in the NRAMP1 gene of the animal which is associated with superior disease resistance. Novel NRAMP1 sequence, assays, and compositions for identifying the presence of absence of these alleles are provided.

27 Claims, 2 Drawing Sheets

GCGTCAGTCTTCCCTGCTCAGAGCCCATGCCCTCTCCACATCCTCTGTGGCAAGAGGCCATCAGG
ATCTGGRGACCTCTGCATTCACATGGAAGGAGAGGAATCCAGAAGGCTCTGCTTCTCACACATCT
TCTGGAAGGTCTGGTCGAGGGATGGATGTGATGGACTGAAGAAAGRAATCAAGGGCTCCTATTCA
GCTGGGGCTTCATTTGCTTTCGCCCTGCCACCAGAAACAGGCAGGTCACTCACCAAGGCTCTTGG
GGCCCCTGG*CAGGTGACACAGGCCCCCCAAAGCAGAGCAGAACCCAATATGGCTCCATCTCCAGC*
*TCACCGAGYCCAGGGCCACCACAAGTACCTCCCGGAGGRACCTACCTGAGTGAGAAGATCCCCAT*
*CCCGAATGCAGAACCGGTGAGAATGCTGGAAACTTCCTGGGGTCTTTTAGGATGGATAGGATCCC*
ATGGGATCTCTCTGGCCAAGGGAGGGAGGTCCCCCGAAGACCAGGGCAAGTCCCTTCCAGATGGA
GAGTGGTAACTGCCGT

*Figure 1*

CATGCTGCTGGTCTGTGCCATCAACTTTTACTTTCTGGTCAGCTACCTGCCCAGCCTCCCCCACC
CCGCCTACTTCGGCCTTGTAGCACTACTGGCTGTCATCTACCTGGGCCTCACCACCTAC*TGGTA*
*CCGTAGTGTCAGCGGGTGCCTTGGGGATGGGGGCAGCACGGAGGGGAGACCATAGATGGAGGGCT*
*GGGGAGGGGGGATACACTGGGGCTTCCCCAAAGGTCTTGTTCTCTCCCCTTCTCATGGTCGCCTC*
*TCCCCCAGGTCTGGACCTGTCTTATCGCCCATGGAGCTACCCTTCTGGTCCACAGTTCCCATCAA*
CACTTTCTGTATGGGCTTCTGGAATAGGAGCAGGAGAAGGAAAAGACCTCGGGATGAGCTACCCT
GCAGGGCTTGGCTGAGGGTGGAATGCGTGGGGCATATTGGCCTGCTGGACAGCTGGGCATGGCGG
GGGACCCRCTGTGTGGAAGCAGCTAGATGGAGCGCAAGTTTTTGGAAGCACGCCAACCTGAGTTC
CTTAGGGACCTGCAGTTTCCTAACTTGGACAAGTTACTCAACCTCTGGATCTCAGTGTCTTCATC
TATAAAATGGGACAACACCAATCTTGCAAT

*Figure 2*

| | | |
|---:|:---|---:|
| 1 | TGAGCCCTTCATTTAACAGAAGAAATAAGCTCAGAGGCAGGACAGGATCT | 50 |
| 51 | GGTGACAACGTCAAATGGATCCATGGTAGAAGCAAGACCAGAATTCCAGG | 100 |
| 101 | ACCCTCTTCTTCAGAGGACCTCCTTAGCCTGGAACTTCAATGCATGTCCC | 150 |
| 151 | CGTGGCCGGGCTTGGAAGGTCTTTTCCTTTGTGGCACTCCTAGGTGGTCA | 200 |
| 201 | TGGGACTCCCTCCCACCCATTAGGCCAACCTGCTGCCATAGGACCCAAG | 250 |
| 251 | GTCAAAAGGAAAAGGGCCTGTTTGTGTGGCGCTGGAGGGTTAGTCGTGT | 300 |
| 301 | GATCTAGAC<u>R</u>TGAATGCTCAAGTGGCAGGAAGCGTCTGAAATCAGAGCTA | 350 |
| 351 | ACTTGGGAGGCAGAAAACTCGGGGTTCCCGGAAGGGAGCCAGAGGGTGGT | 400 |
| 401 | GCGAGGCTCACGCCAGGAGGGGAATGAAAGCCTGTTCTGTGGCCACCCAG | 450 |
| 451 | ACCCTTCCGTCAGAGCTGGCCACTTCTGCCTTTGGAAAGTGTTTCACAAT | 500 |
| 501 | GCCCCGGGCATGTGTGAGGACAGCCAAGTTGAGCTGAAGATGCGTAAAAG | 550 |
| 551 | GCTATAGACCCACACACTCACCGGTTCCCAGAGAGGACGGGTGGACCAGA | 600 |
| 601 | GAGCCACCCAGCACACCACTCACACAGAGAGCATCTGAGTCTGTGGTCCT | 650 |
| 651 | CATGACAGGTGAGTAGCCCCCTCTGTCCAGGGACAGAGCCTGGATTGGAG | 700 |
| 701 | CAGGAGGAGAGCATCAGGAGGGGCAAGGGAAGCCCC<u>R</u>GGTCCCTGTGGG | 750 |
| 751 | AGTCCTGGTCTTGACCACAATTCTGGACAGGAGCCTGGGGTCAGGCGCTT | 800 |
| 801 | CACGTTGCCAAGGGCAGAGCCTCCCCCTGCCTCATCTCTGTGGGTTTGA | 850 |
| 851 | ACCTCTGGGGTTTCCCTGGAAGCTGGAGGCAGGGATGAGACCAAAGGACA | 900 |
| 901 | CACACGTTGGCGTCAGTCTTCCCTGCTCAGAGCC | |

*Figure 3*

GENETIC MARKERS FOR SCREENING ANIMALS FOR IMPROVED DISEASE RESISTANCE (NRAMP)

CROSS-REFERENCE TO RELATED APPLICATIONS

This application claims benefit under 35 U.S.C. §119(e) of provisional application 60/294,757 filed May 31, 2001.

GRANT REFERENCE

Work for this invention was funded in part by ISU Grant No. 400-43-71-21-3337. The Government may have certain rights in this invention.

FIELD OF THE INVENTION

This invention relates generally to the detection of genetic differences among animals. More particularly, the invention relates to genetic markers which have been identified in several genes indicative of heritable phenotypes associated with improved traits, such as disease resistance and innate immunity. Methods and compositions for use of these markers in genotyping of animals and selection are also disclosed.

BACKGROUND OF THE INVENTION

Genetic differences exist among individual animals as well as among breeds which can be exploited by breeding techniques to achieve animals with desirable characteristics. For example, Chinese pig breeds are known for reaching puberty at an early age and for their large litter size, while American breeds are known for their greater growth rates and leanness. Often, however, heritability for desired traits is low, and standard breeding methods which select individuals based upon phenotypic variations do not take fully into account genetic variability or complex gene interactions which exist.

There is a continuing need for an approach that deals with selection for disease resistance at the cellular or DNA level. This method will provide the ability to genetically evaluate animals and to enable breeders to more accurately select those animals which not only phenotypically express desirable traits but those which express favorable underlying genetic criteria. This has largely been accomplished to date by marker-assisted selection.

RFLP analysis has been used by several groups to study pig DNA. Jung et al., Theor. Appl. Genet., 77:271–274 (1989), incorporated herein by reference, discloses the use of RFLP techniques to show genetic variability between two pig breeds. Polymorphism was demonstrated for swine leukocyte antigen (SLA) Class I genes in these breeds. Hoganson et al., Abstract for Annual Meeting of Midwestern Section of the American Society of Animal Science, Mar. 26–28, 1990, incorporated herein by reference, reports on the polymorphism of swine major histocompatibility complex (MHC) genes for Chinese pigs, also demonstrated by RFLP analysis. Jung et al. Animal Genetics, 26:79–91 (1989), incorporated herein by reference, reports on RFLP analysis of SLA Class I genes in certain boars. The authors state that the results suggest that there may be an association between swine SLA/MHC Class I genes and production and performance traits. They further state that the use of SLA Class I restriction fragments, as genetic markers, may have potential in the future for improving pig growth performance.

The ability to follow a specific favorable genetic allele involves a novel and lengthy process of the identification of a DNA molecular marker for a major effect gene. The marker may be linked to a single gene with a major effect or linked to a number of genes with additive effects. DNA markers have several advantages; segregation is easy to measure and is unambiguous, and DNA markers are co-dominant, i.e., heterozygous and homozygous animals can be distinctively identified. Once a marker system is established, selection decisions could be made very easily, since DNA markers can be assayed any time after a tissue or blood sample can be collected from the individual infant animal, or even an embryo.

The use of genetic differences in receptor genes has become a valuable marker system for selection. For example, U.S. Pat. Nos. 5,550,024 and 5,374,526, issued to Rothschild et al., disclose a polymorphism in the pig estrogen receptor gene which is associated with larger litter size, the disclosure of which is incorporated herein by reference. U.S. Pat. No. 5,935,784 discloses polymorphic markers in the pig prolactin receptor gene which are associated with larger litter size and overall reproductive efficiency, the disclosure of which is incorporated herein by reference.

NRAMP1 Gene

The NRAMP1 gene was isolated from a murine Bcg candidate gene and designated "natural resistance-associated macrophage protein" gene by Vidal and coworkers (Vidal, et al., Natural resistance to infection with intracellular parasites: isolation of a candidate for Bcg. Cell 73, 469–485 (1993)). Bcg was found during genetic studies of mice to mediate antimicrobial activity of macrophages against intracellular parasites early during infection. The isolated NRAMP1 gene apparently encodes an integral membrane protein that has structural features similar to prokaryotic and eukaryotic ion transporters. More recent studies using knockout mice (Vidal, et al., J. Exp. Med. 182:655–666 (1995)) indicated the NRAMP1 is the Bcg/Lsh/Ity gene (3 genes capable of controlling resistance and susceptibility to *Mycobacterium bovis* (BCG), *Leishmania donovani* and *Salmonella typhimurium*, respectively, known genetically to be a single gene expressed at the macrophage level, Blackwell, J. M. The macrophage resistance gene Lsh/Ity/Bcg. Res. Immunol. 140: 767 (1989)). It has been suggested that the murine NRAMP1 protein might function in phagolysosomal membranes as a concentrator of nitric oxide, mediating cytocidal activity against the ingested parasites of infected macrophage (Vidal, et al. 1993; Malo, et al. Genetic control of host resistance to infection. TIG 10, 365–371 (1994); Cellier, et al. Human natural resistance-associated macrophage protein: cDNA cloning, chromosomal mapping, genomic organization, and tissue-specific expression. J. Exp. Med. 180, 1741–1752 (1994); Malo, et al Haplotype mapping and sequence analysis of the mouse NRAMP1 gene predicts susceptibility to infection with intracellular parasites. Genomics 23, 51–61 (1994)). It has recently been indicated that the mammalian NRAMP protein family (at least NRAMP 2) functions as broad specificity divalent cation transporters (Gunshin, et al. Nature 388: 482, 1997; Fleming, et al. Nature Genet. 16: 383, 1997). A cDNA for NRAMP1 was isolated from a pre B-cell cDNA library and sequenced. The amino acid sequence for the protein product was deduced from the nucleotide sequence and predicts a 53 kDa protein. On the basis of the deduced amino acid sequence, Vidal et al. (1993) proposed as a function of the NRAMP1 protein the transport of nitrate across the membrane of the intracellular vacuole of the macrophage containing the microorganisms. In the acid environment of this vacuole, the nitrate could be converted via nitrite to toxic nitric oxide thereby enhancing killing of the microorganisms. The NRAMP1 protein has been localized to the phagolysosomal membrane, and with the data on NRAMP2 function, an alternative function has recently been proposed. It is known that bacteria use superoxide dismutase (SOD) to detoxify the phagolysosome. SOD requires divalent cations, notably $Mn^{++}$. It is proposed that NRAMP1 may pump metal ions (such as $Fe^{++}$ or $Mn^{++}$) out of the phagolysosome compartment, thus depriving bacteria of this defense mechanism (G. Govoni and P. Gros (1998) Inflamm. Res. 47:277–284).

Nucleotide sequence analyses of murine NRAMP1 cDNA showed that the susceptible phenotype was associated with a nonconservative glycine-to-aspartic acid amino acid substitution within the second trans membrane domain of the protein (Vidal, et al. 1993).

Whatever the mechanism of NRAMP1, it has been recognized as important for its role in infection resistance in several other species, in addition to mice. Its homologues, variants and polymorphisms have been investigated in humans and agriculturally important animals, with unpredictable results for use of these variants as markers of any phenotype. For example, see, international application WO 95/13371 to Gros et al.

Gros et al. discloses mouse and human cDNAs from NRAMP1 genes. The nucleotide sequences of mouse and human cDNAs are disclosed, as are the amino acid sequences. Throughout the document a potential use for the nucleotide sequences is disclosed as assaying for different mutations or variability which is associated with susceptibility or resistance to infectious diseases including tuberculosis, leprosy, salmonellosis, and leshmaniasis.

The application discloses isolation of the mouse gene from a library and the identification of two alternate forms $Bcg^r$ and $Bcg^s$, which had a single nucleotide difference, namely, a guanine at nucleotide 783, which was present in resistant strains. Importantly, however, there were two additional silent mutations detected in the 5' portion of the transcript from a resistant mice strain, one at nucleotide position 563 and another at nucleotide position 1169 which did not have any different phenotypic effect. Out of all polymorphisms detected in the tested strains, four out of five polymorphisms identified were silent mutations and were not shown to be associated with any difference in susceptibility to infection.

Application number WO 98/12353 to Templeton et al. discloses identification and sequencing of homologues of murine NRAMP1 from bovine, bison and other artiodactyla. The invention discloses particular sequences of NRAMP1 which correlate with resistance or susceptibility to brucellosis, tuberculosis, paratuberculosis and salmonellosis in cattle. The sequence associated with resistance/susceptibility is a transversion at position 1782 of the NRAMP1 cDNA and a polymorphic DNA microsatellite sequence difference.

The examples section discloses cloning of bovine NRAMP1 and isolation of bovine NRAMP1 cDNA, analysis of predicted bovine NRAMP1 structure, genetic mapping of bovine NRAMP1, single-stranded conformational analysis disclosing the microsatellite length polymorphism, cell specific expression of bovine NRAMP1 mRNA, SSCA disclosing a 3' untranslated region polymorphism, and association of resistances or susceptibility to ruminant brucellosis, tuberculosis, paratuberculosis and salmonellosis, with the alternative gene forms.

The Barton et al. application, WO 95/20044, discloses the sequence of NRAMP1 gene isolated from mice. Function and uses of the gene include diagnosing the susceptibility or resistance to microorganisms including *Salmonella typhimurium*, *Leishmania donovani* and *Mycobacterium bovis*. A resistant allele of murine NRAMP1 was found with two silent mutations, one at 359 base pairs and one at 965 base pairs. In humans a polymorphic repeat in the 5' promoter region was identified, with no association with a useful trait disclosed.

The Rotter et al. reference (WO 99/23255) relates to a method of identifying novel alleles or allelic combinations in the human NRAMP1 locus which evidence statistically significant correlation with one or more biological responses (humans with diseases), such as Crohn's Disease, Ulcerative Colitis or their subtypes. Seven alleles of the NRAMP1 satellite marker were studied. The D2S434 allele is characterized by seven different fragment sizes from 262 base pairs to 286 base pairs characterized by repeats of GATA(N). The 2DS1323 NRAMP1 allele was identified in two forms of GATA(N) repeats, one of 324 base pairs and one of 328 base pairs. The D2S1323 polymorphism and D2S434 polymorphism were analyzed for linkage to various diseases. Three mutated and wild type NRAMP1 DNA sequences were also obtained from patients, and associations for some of the alleles were found with inflammatory bowel disease and ulcerative colitis.

As can be seen, the NRAMP1 gene is known to be variable and it is highly unpredictable as to which if any variations are associated with useful traits to be of value as a genetic marker.

The present invention provides a genetic markers, based upon the discovery of a polymorphisms in the porcine NRAMP1 gene, which correlate with resistance or susceptibility to pathogenic infection in pigs. This will permit genetic typing of pigs for their NRAMP1 allele and for determination of the relationship of specific RFLPs to resistance to infection. It will also permit the identification of individual males and females that carry the gene for improved resistance. Thus, the markers may be selection tools in breeding programs to develop lines and breeds that produce litters containing more resistant offspring. Also disclosed are novel porcine NRAMP1 genomic sequences, as well as primers for assays to identify the presence or absence of marker alleles.

According to the invention a polymorphism was identified in the NRAMP1 gene which is associated with the improved resistance to pathogenic infection.

It is an object of the invention to provide a method of screening pigs to determine those more likely to produce offspring with improved pathogenic resistance, in the NRAMP1 gene.

Another object of the invention is to provide a method for identifying genetic markers for improved disease resistance.

A further object of the invention is to provide genetic markers for selection and breeding to obtain pigs that will be expected to have a lower susceptibility to infection than those without the favorable allele.

Yet another object of the invention is to provide a kit for evaluating a sample of pig DNA for specific genetic markers of disease resistance.

Additional objects and advantages of the invention will be set forth in part in the description that follows, and in part will be obvious from the description, or may be learned by the practice of the invention. The objects and advantages of the invention will be attained by means of the instrumentality's and combinations particularly pointed out in the appended claims.

SUMMARY OF THE INVENTION

To achieve the objects and in accordance with the purpose of the invention, as embodied and broadly described herein, the present invention provides a method for screening animals to determine those more likely to have biologically different phenotypes such as, or associated with, improved innate immunity, disease resistance or resistance to bacterial infection, as evidenced by factors including but not limited to bacterial count, lymphocyte count, neutrophil count, or monocyte count after challenge to identify animals which have superior bacterial killing, or ability to stave off infection in a particular population, when bred, or raised or to select against pigs which have alleles indicating unfavorable phenotypes. These traits also may be observed by assaying for traits associated with overall improved health. As used herein the term "disease resistance" or "innate immunity" shall mean an ability to stave off infection that is biologically different to that which is observed when the favorable allele is not present as evidenced by measurements included but not limited to average lymphocyte count and percentage, monocyte count, neutrophil count and percentage and bacterial count after challenge or other measurements of innate immunity. This can include other indicia of animals associated with a good immune system and overall health such as weight gain, feed efficiency, or other indicia of overall health of animals.

Thus, the present invention provides a method for screening pigs to determine those more likely to have the improved trait of superior disease resistance and/or those less likely to demonstrate those traits which method comprises the steps: 1) obtaining a sample of tissue or genomic DNA from an animal; and 2) analyzing the mRNA or genomic DNA obtained in 1) to determine which allele(s) is/are present. Briefly, the sample of genetic material analyzed to determine the presence or absence of a particular allele that is correlated with a desirable trait, or one which is linked thereto.

As is well known to those of skill in the art, a variety of techniques may be utilized when comparing nucleic acid molecules for sequence differences. These include by way of example, restriction fragment length polymorphism analysis, heteroduplex analysis, single strand conformation polymorphism analysis, denaturing gradient electrophoresis and temperature gradient electrophoresis.

In one embodiment, the polymorphism is a restriction fragment length polymorphism (RFLP) and the assay comprises identifying the gene from isolated genetic material; exposing the gene to a restriction enzyme that yields restriction fragments of the gene of varying length; separating the restriction fragments to form a restriction pattern, such as by electrophoresis or HPLC separation; and comparing the resulting restriction fragment pattern from an animal gene that is either known to have or not to have the desired marker. If an animal tests positive for the marker (or allele), such animal can be considered for inclusion in the breeding program. If the animal does not test positive for the marker genotype, the animal can be culled from the group and otherwise used.

In a most preferred embodiment, the gene, or a fragment thereof, is isolated by the use of primers and DNA polymerase to amplify a specific region of the gene which contains the polymorphism or a polymorphism linked thereto. Next, the amplified region is either directly separated or sequenced or is digested with a restriction enzyme and fragments are again separated. Visualization of the separated fragments, or RFLP pattern, is by simple staining of the fragments, or by labeling the primers or the nucleoside triphosphates used in amplification.

In another embodiment, the invention comprises a method for identifying a genetic marker for disease resistance traits, such as bacterial counts, lymphocyte count, neutrophil count, or monocyte count after challenge. Male and female animals of the same breed, breed cross, or similar genetic lineage are bred, and the disease resistance traits are determined. A polymorphism in the gene of each animal is identified and associated with the desired trait(s). Preferably, PCR-RFLP analysis is used to determine the polymorphism.

It is also possible to establish linkage between specific alleles of alternative DNA markers and alleles of DNA markers known to be associated with a particular gene (e.g., the NRAMP1 gene discussed herein) which have previously been shown to be associated with a particular trait. Thus, in the present situation, taking a particular gene, it would be possible, at least in the short term, to select for pigs, or other animals, likely to have superior disease resistance or ability to stave off infection, or alternatively, against pigs likely to have inferior traits, indirectly, by selecting for certain alleles of a particular gene associated with the marker alleles through the selection of specific linked alleles of alternative chromosome markers. Thus, in the present situation, taking the NRAMP1 gene, it would be possible, at least in the short term, to select for pigs likely to produce disease resistance, or alternatively, against pigs likely to produce susceptible litters indirectly, by selecting for certain alleles of the NRAMP1 associated marker through the selection of specific alleles of alternative markers located on chromosome 15 as NRAMP1 is. See Sun et al., *Animal Genetics*, 1998, 29:138–140 for mapping of NRAMP1 and linkage. According to the invention, examples of markers on the published PiGMaP chromosome 15 map which are linked to the NRAMP1 gene are S0149, S0784, S0088, and DPP4.

The invention further comprises a kit for evaluating a sample of DNA for the presence in genetic material of a desired genetic marker located in the gene indicative of a inheritable trait of disease resistance or ability to stave off infection. At a minimum, the kit is a container with one or more reagents that identify a polymorphism in the porcine NRAMP1 gene. Preferably, the reagent is a set of oligonucleotide primers capable of amplifying a fragment of the selected gene that contains a polymorphism. Preferably, the kit further contains a restriction enzyme that cleaves the gene in at least one place, allowing for separation of fragments and detection of polymorphic loci.

DETAILED DESCRIPTION OF THE FIGURES

FIG. 1 is the 536 bp PCR product (SEQ ID NO: 3) amplified with SEQ ID NOS: 1 and 2 primers. Exon 2 sequence is in italic text. Primers are shown in bold (forward sequence of the 5' primer and reverse complement of the 3' primer sequence is shown).

FIG. 2 is the 615 bp PCR product (SEQ ID NO: 4) amplified with SEQ ID NOS: 5 and 6 primers. The primers again are in bold spanning exon 14–15 (forward sequence of the 5' primer and reverse complement of the 3' primer sequence is shown). Intron 14 is in italics.

FIG. 3 is the 934 bp PCR product (SEQ ID NO: 7) amplified with SEQ ID NOS: 8 and 9 primers. The primers again are in bold (forward sequence of the 5' primer and reverse complement of the 3' primer sequence is shown).

DETAILED DESCRIPTION OF THE INVENTION

Reference will now be made in detail to the presently preferred embodiments of the invention, which together with the following examples, serve to explain the principles of the invention. All references cited herein are hereby expressly incorporated by reference.

The invention relates to the identification of quantitative trait loci (QTL) for improved disease resistance or resistance to pathogen infection, including, but not limited to, Salmonellosis, identifiable by traits such as bacterial count, total or specific leukocyte counts (including white blood cells, lymphocytes, monocytes, neutrophils) before and/or after infection, or leukocyte function to identify pigs and other animals which have superior pathogen killing or ability to stave off infection. It provides a method of screening animals to determine those more likely to have improved resistance and/or good immune system and overall health traits (as shown by measures such as weight gain or feed efficiency) when bred by identifying the presence or an absence of a polymorphism in certain genes (NRAMP1) that are correlated with these traits.

Thus, the invention relates to genetic markers and methods of identifying those markers in a pig or other animal of a particular breed, strain, population, or group, whereby an animal has disease resistance above the mean for that particular breed, strain, population, or group.

The marker may be identified by any method known to one of ordinary skill in the art which identifies the presence or absence of the particular allele or marker, including, for example, direct sequencing single-strand conformation polymorphism analysis (SSCP), base excision sequence scanning (BESS), RFLP analysis, heteroduplex analysis, denaturing gradient gel electrophoresis, allelic PCR, temperature gradient electrophoresis, ligase chain reaction, direct sequencing, minisequencing, nucleic acid hybridization, and micro-array-type detection of the NRAMP1 gene, or other linked sequences, and examination for a polymorphic site. Yet another technique includes an Invader Assay which includes isothermic amplification that relies on a catalytic release of fluorescence. See Third Wave Technology at www.twt.com. All of these techniques are intended to be within the scope of the invention. A brief description of these techniques follows.

Isolation and Amplification of Nucleic Acid

Samples of patient, proband, test subject, or family member genomic DNA are isolated from any convenient source including saliva, buccal cells, hair roots, blood, cord blood, amniotic fluid, interstitial fluid, peritoneal fluid, chorionic villus, and any other suitable cell or tissue sample with intact interphase nuclei or metaphase cells. The cells can be obtained from solid tissue as from a fresh or preserved organ or from a tissue sample or biopsy. The sample can contain compounds which are not naturally intermixed with the biological material such as preservatives, anticoagulants, buffers, fixatives, nutrients, antibiotics, or the like.

Methods for isolation of genomic DNA from these various sources are described in, for example, Kirby, DNA Fingerprinting, An Introduction, W. H. Freeman & Co. New York (1992). Genomic DNA can also be isolated from cultured primary or secondary cell cultures or from transformed cell lines derived from any of the aforementioned tissue samples.

Samples of patient, proband, test subject or family member RNA can also be used. RNA can be isolated from tissues expressing the NRAMP1 gene as described in Sambrook et al., supra. RNA can be total cellular RNA, mRNA, poly A+ RNA, or any combination thereof. For best results, the RNA is purified, but can also be unpurified cytoplasmic RNA. RNA can be reverse transcribed to form DNA which is then used as the amplification template, such that the PCR indirectly amplifies a specific population of RNA transcripts. See, e.g., Sambrook, supra, Kawasaki et al., Chapter 8 in PCR Technology, (1992) supra, and Berg et al., Hum. Genet. 85:655–658 (1990).

PCR Amplification

The most common means for amplification is polymerase chain reaction (PCR), as described in U.S. Pat. Nos. 4,683,195, 4,683,202, 4,965,188 each of which is hereby incorporated by reference. If PCR is used to amplify the target regions in blood cells, heparinized whole blood should be drawn in a sealed vacuum tube kept separated from other samples and handled with clean gloves. For best results, blood should be processed immediately after collection; if this is impossible, it should be kept in a sealed container at 4° C. until use. Cells in other physiological fluids may also be assayed. When using any of these fluids, the cells in the fluid should be separated from the fluid component by centrifugation.

Tissues should be roughly minced using a sterile, disposable scalpel and a sterile needle (or two scalpels) in a 5 mm Petri dish. Procedures for removing paraffin from tissue sections are described in a variety of specialized handbooks well known to those skilled in the art.

To amplify a target nucleic acid sequence in a sample by PCR, the sequence must be accessible to the components of the amplification system. One method of isolating target DNA is crude extraction which is useful for relatively large samples. Briefly, mononuclear cells from samples of blood, amniocytes from amniotic fluid, cultured chorionic villus cells, or the like are isolated by layering on sterile Ficoll-Hypaque gradient by standard procedures. Interphase cells are collected and washed three times in sterile phosphate buffered saline before DNA extraction. If testing DNA from peripheral blood lymphocytes, an osmotic shock (treatment of the pellet for 10 sec with distilled water) is suggested, followed by two additional washings if residual red blood cells are visible following the initial washes. This will prevent the inhibitory effect of the heme group carried by hemoglobin on the PCR reaction. If PCR testing is not performed immediately after sample collection, aliquots of $10^6$ cells can be pelleted in sterile Eppendorf tubes and the dry pellet frozen at −20° C. until use.

The cells are resuspended ($10^6$ nucleated cells per 100 $\mu$l) in a buffer of 50 mM Tris-HCl (pH 8.3), 50 mM KCl 1.5 mM $MgCl_2$, 0.5% TWEEN 20 (also known generically as Polysorbrate 20), 0.5% NP40 (NONIDET P40) supplemented with 100 $\mu$g/ml of proteinase K. After incubating at 56° C. for 2 hr. the cells are heated to 95° C. for 10 min to inactivate the proteinase K and immediately moved to wet ice (snap-cool). If gross aggregates are present, another cycle of digestion in the same buffer should be undertaken. Ten $\mu$l of this extract is used for amplification.

When extracting DNA from tissues, e.g., chorionic villus cells or confluent cultured cells, the amount of the above mentioned buffer with proteinase K may vary according to the size of the tissue sample. The extract is incubated for 4–10 hrs at 50°–60° C. and then at 95° C. for 10 minutes to inactivate the proteinase. During longer incubations, fresh proteinase K should be added after about 4 hr at the original concentration.

When the sample contains a small number of cells, extraction may be accomplished by methods as described in Higuchi, "Simple and Rapid Preparation of Samples for PCR", in PCR Technology, Ehrlich, H. A. (ed.), Stockton Press, New York, which is incorporated herein by reference. PCR can be employed to amplify target regions in very small numbers of cells (1000–5000) derived from individual colonies from bone marrow and peripheral blood cultures. The cells in the sample are suspended in 20 $\mu$l of PCR lysis buffer (10 mM Tris-HCl (pH 8.3), 50 mM KCl, 2.5 mM $MgCl_2$, 0.1 mg/ml gelatin, 0.45% NP40, 0.45% TWEEN 20) and frozen until use. When PCR is to be performed, 0.6 µl of proteinase K (2 mg/ml) is added to the cells in the PCR lysis buffer. The sample is then heated to about 60° C. and incubated for 1 hr. Digestion is stopped through inactivation of the proteinase K by heating the samples to 95° C. for 10 min and then cooling on ice.

A relatively easy procedure for extracting DNA for PCR is a salting out procedure adapted from the method described by Miller et al., Nucleic Acids Res. 16:1215 (1988), which is incorporated herein by reference. Mononuclear cells are separated on a Ficoll-Hypaque gradient. The cells are resuspended in 3 ml of lysis buffer (10 mM Tris-HCl, 400 mM NaCl, 2 mM $Na_2$ EDTA, pH 8.2). Fifty µl of a 20 mg/ml solution of proteinase K and 150 µl of a 20% SDS solution are added to the cells and then incubated at 37° C. overnight. Rocking the tubes during incubation will improve the digestion of the sample. If the proteinase K digestion is incomplete after overnight incubation (fragments are still visible), an additional 50 µl of the 20 mg/ml proteinase K solution is mixed in the solution and incubated for another night at 37° C. on a gently rocking or rotating platform. Following adequate digestion, one ml of a 6M NaCl solution is added to the sample and vigorously mixed. The resulting solution is centrifuged for 15 minutes at 3000 rpm. The pellet contains the precipitated cellular proteins, while the supernatant contains the DNA. The supernatant is removed to a 15 ml tube that contains 4 ml of isopropanol. The contents of the tube are mixed gently until the water and the alcohol phases have mixed and a white DNA precipitate has formed. The DNA precipitate is removed and dipped in a solution of 70% ethanol and gently mixed. The DNA precipitate is removed from the ethanol and air-dried. The precipitate is placed in distilled water and dissolved.

Kits for the extraction of high-molecular weight DNA for PCR include a Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N.H.), DNA Extraction Kit (Stratagene, LaJolla, Calif.), TurboGen Isolation Kit (Invitrogen, San Diego, Calif.), and the like. Use of these kits according to the manufacturer's instructions is generally acceptable for purification of DNA prior to practicing the methods of the present invention.

The concentration and purity of the extracted DNA can be determined by spectrophotometric analysis of the absorbance of a diluted aliquot at 260 nm and 280 nm. After extraction of the DNA, PCR amplification may proceed. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In a particularly useful embodiment of PCR amplification, strand separation is achieved by heating the reaction to a sufficiently high temperature for a sufficient time to cause the denaturation of the duplex but not to cause an irreversible denaturation of the polymerase (see U.S. Pat. No. 4,965,188, incorporated herein by reference). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, CSH-Quantitative Biology, 43:63–67; and Radding, 1982, Ann. Rev. Genetics 16:405–436, each of which is incorporated herein by reference.

Template-dependent extension of primers in PCR is catalyzed by a polymerizing agent in the presence of adequate amounts of four deoxyribonucleotide triphosphates (typically dATP, dGTP, dCTP, and dTTP) in a reaction medium comprised of the appropriate salts, metal cations, and pH buffering systems. Suitable polymerizing agents are enzymes known to catalyze template-dependent DNA synthesis. In some cases, the target regions may encode at least a portion of a protein expressed by the cell. In this instance, mRNA may be used for amplification of the target region. Alternatively, PCR can be used to generate a cDNA library from RNA for further amplification, the initial template for primer extension is RNA. Polymerizing agents suitable for synthesizing a complementary, copy-DNA (cDNA) sequence from the RNA template are reverse transcriptase (RT), such as avian myeloblastosis virus RT, Moloney murine leukemia virus RT, or Thermus thermophilus (Tth) DNA polymerase, a thermostable DNA polymerase with reverse transcriptase activity marketed by Perkin Elmer Cetus, Inc. Typically, the genomic RNA template is heat degraded during the first denaturation step after the initial reverse transcription step leaving only DNA template. Suitable polymerases for use with a DNA template include, for example, *E. coli* DNA polymerase I or its Klenow fragment, T4 DNA polymerase, Tth polymerase, and Taq polymerase, a heat-stable DNA polymerase isolated from Thermus aquaticus and commercially available from Perkin Elmer Cetus, Inc. The latter enzyme is widely used in the amplification and sequencing of nucleic acids. The reaction conditions for using Taq polymerase are known in the art and are described in Gelfand, 1989, PCR Technology, supra.

Allele Specific PCR

Allele-specific PCR differentiates between target regions differing in the presence of absence of a variation or polymorphism. PCR amplification primers are chosen which bind only to certain alleles of the target sequence. This method is described by Gibbs, Nucleic Acid Res. 17:12427–2448 (1989).

Allele Specific Oligonucleotide Screening Methods

Further diagnostic screening methods employ the allele-specific oligonucleotide (ASO) screening methods, as described by Saiki et al., Nature 324:163–166 (1986). Oligonucleotides with one or more base pair mismatches are generated for any particular allele. ASO screening methods detect mismatches between variant target genomic or PCR amplified DNA and non-mutant oligonucleotides, showing decreased binding of the oligonucleotide relative to a mutant oligonucleotide. Oligonucleotide probes can be designed that under low stringency will bind to both polymorphic forms of the allele, but which at high stringency, bind to the allele to which they correspond. Alternatively, stringency conditions can be devised in which an essentially binary response is obtained, i.e., an ASO corresponding to a variant form of the target gene will hybridize to that allele, and not to the wildtype allele.

Ligase Mediated Allele Detection Method

Target regions of a test subject's DNA can be compared with target regions in unaffected and affected family members by ligase-mediated allele detection. See Landegren et al., Science 241:107–1080 (1988). Ligase may also be used to detect point mutations in the ligation amplification reaction described in Wu et al., Genomics 4:560–569 (1989). The ligation amplification reaction (LAR) utilizes amplification of specific DNA sequence using sequential rounds of template dependent ligation as described in Wu, supra, and Barany, Proc. Nat. Acad. Sci. 88:189–193 (1990).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature (TM). Melting domains are at least 20 base pairs in length, and may be up to several hundred base pairs in length.

Differentiation between alleles based on sequence specific melting domain differences can be assessed using polyacrylamide gel electrophoresis, as described in Chapter 7 of Erlich, ed., PCR Technology, Principles and Applications for DNA Amplification, W. H. Freeman and Co., New York (1992), the contents of which are hereby incorporated by reference.

Generally, a target region to be analyzed by denaturing gradient gel electrophoresis is amplified using PCR primers flanking the target region. The amplified PCR product is applied to a polyacrylamide gel with a linear denaturing gradient as described in Myers et al., Meth. Enzymol. 155:501–527 (1986), and Myers et al., in Genomic Analysis, A Practical Approach, K. Davies Ed. IRL Press Limited, Oxford, pp. 95–139 (1988), the contents of which are hereby incorporated by reference. The electrophoresis system is maintained at a temperature slightly below the Tm of the melting domains of the target sequences.

In an alternative method of denaturing gradient gel electrophoresis, the target sequences may be initially attached to a stretch of GC nucleotides, termed a GC clamp, as described in Chapter 7 of Erlich, supra. Preferably, at least 80% of the nucleotides in the GC clamp are either guanine or cytosine. Preferably, the GC clamp is at least 30 bases long. This method is particularly suited to target sequences with high Tm's.

Generally, the target region is amplified by the polymerase chain reaction as described above. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions as described above. DNA fragments differing by a single base change will migrate through the gel to different positions, which may be visualized by ethidium bromide staining.

Temperature Gradient Gel Electrophoresis

Temperature gradient gel electrophoresis (TGGE) is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tTGGE) uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis.

Single-strand Conformation Polymorphism Analysis

Target sequences or alleles at the NRAMP1 locus can be differentiated using single-strand conformation polymorphism analysis, which identifies base differences by alteration in electrophoretic migration of single stranded PCR products, as described in Orita et al., Proc. Nat. Acad. Sci. 85:2766–2770 (1989). Amplified PCR products can be generated as described above, and heated or otherwise denatured, to form single stranded amplification products. Single-stranded nucleic acids may refold or form secondary structures which are partially dependent on the base sequence. Thus, electrophoretic mobility of single-stranded amplification products can detect base-sequence difference between alleles or target sequences.

Chemical or Enzymatic Cleavage of Mismatches

Differences between target sequences can also be detected by differential chemical cleavage of mismatched base pairs, as described in Grompe et al., Am. J. Hum. Genet. 48:212–222 (1991). In another method, differences between target sequences can be detected by enzymatic cleavage of mismatched base pairs, as described in Nelson et al., Nature Genetics 4:11–18 (1993). Briefly, genetic material from a patient and an affected family member may be used to generate mismatch free heterohybrid DNA duplexes. As used herein, "heterohybrid" means a DNA duplex strand comprising one strand of DNA from one person, usually the patient, and a second DNA strand from another person, usually an affected or unaffected family member. Positive selection for heterohybrids free of mismatches allows determination of small insertions, deletions or other polymorphisms that may be associated with alterations in androgen metabolism.

Non-PCR Based DNA Diagnostics

The identification of a DNA sequence linked to NRAMP1 can be made without an amplification step, based on polymorphisms including restriction fragment length polymorphisms in a patient and a family member. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes are preferably labeled directly or indirectly, such that by assaying for the presence or absence of the probe, one can detect the presence or absence of the target sequence. Direct labeling methods include radioisotope labeling, such as with 32P or 35S. Indirect labeling methods include fluorescent tags, biotin complexes which may be bound to avidin or streptavidin, or peptide or protein tags. Visual detection methods include photoluminescents, Texas red, rhodamine and its derivatives, red leuco dye and e, e', 5, 5'-5354amethylbenzidine (TMB), fluorescein, and its derivatives, dansyl, umbelliferone and the like or with horse radish peroxidase, alkaline phosphatase and the like.

Hybridization probes include any nucleotide sequence capable of hybridizing to the porcine chromosome where NRAMP1 resides, and thus defining a genetic marker linked to NRAMP, including a restriction fragment length polymorphism, a hypervariable region, repetitive element, or a variable number tandem repeat. Hybridization probes can be any gene or a suitable analog. Further suitable hybridization probes include exon fragments or portions of cDNAs or genes known to map to the relevant region of the chromosome.

Preferred tandem repeat hybridization probes for use according to the present invention are those that recognize a small number of fragments at a specific locus at high stringency hybridization conditions, or that recognize a larger number of fragments at that locus when the stringency conditions are lowered.

One or more additional restriction enzymes and/or probes and/or primers can be used. Additional enzymes, constructed probes, and primers can be determined by routine experimentation by those of ordinary skill in the art and are intended to be within the scope of the invention.

Although the methods described herein may be in terms of the use of a single restriction enzyme and a single set of primers, the methods are not so limited. One or more additional restriction enzymes and/or probes and/or primers can be used, if desired. Additional enzymes, constructed probes and primers can be determined through routine experimentation, combined with the teachings provided and incorporated herein.

Genetic markers for genes are determined as follows. Male and female animals of the same breed or breed cross or derived from similar genetic lineages are mated. The offspring with the beneficial trait are determined. RFLP analysis of the parental DNA is conducted as discussed above in order to determine polymorphisms in the selected gene of each animal. The polymorphisms are associated with the traits.

When this analysis is conducted and the polymorphism is determined by RFLP or other analysis, amplification primers may be designed using analogous human or other closely related animal known sequences. The sequences of many of the genes have high homology. Primers may also be designed using known gene sequences as exemplified in Genbank or even designed from sequences obtained from linkage data from closely surrounding genes. According to the invention, sets of primers have been selected which identify regions in polymorphic genes. The polymorphic fragments have been shown to be alleles, and each was shown to be associated with beneficial traits, such as disease resistance, for various breeds. Often genotype associated with this trait alternates for different breeds. This outcome is similar to the situation disclosed in U.S. Pat. No. 5,374,523 entitled "Allelic variants of Bovine Somatotropin gene: Genetic marker for Superior Milk Production in Bovine" where the inventor found an allelic polymorphism in the somatotropin gene and one allelic form was beneficial for jersey cows and the alternate form was beneficial for Holstein cows.

The reagents suitable for applying the methods of the invention may be packaged into convenient kits. The kits provide the necessary materials, packaged into suitable containers. At a minimum, the kit contains a reagent that identifies a polymorphism in the selected gene that is associated with a trait. Preferably, the reagent is a PCR set (a set of primers, DNA polymerase and 4 nucleoside triphosphates) that hybridize with the gene or a fragment thereof. Preferably, the PCR set is included in the kit.

Preferably, the kit further comprises additional means, such as reagents, for detecting or measuring the detectable entity or providing a control. Other reagents used for hybridization, prehybridization, DNA extraction, visualization etc. may also be included, if desired.

The methods and materials of the invention may also be used more generally to evaluate animal DNA, to identify analogous polymorphisms in animals other than those for whom sequences have been disclosed herein, genetically type individual animals, and detect genetic differences in animals.

In particular, a sample of genomic DNA may be evaluated by reference to one or more controls to determine if a polymorphism in the gene is present. Preferably, RFLP analysis is performed with respect to the gene, and the results are compared with a control. The control is the result of a RFLP analysis of the gene of a different animal where the polymorphism of the gene is known. Similarly, the genotype of an animal may be determined by obtaining a sample of its mRNA or genomic DNA, conducting RFLP analysis of the gene in the DNA, and comparing the results with a control. Again, the control is the result of RFLP analysis of the same gene of a different animal. The results genetically type the animal by specifying the polymorphism in its selected gene. Finally, genetic differences among animals can be detected by obtaining samples of the mRNA or genomic DNA from at least two animals, identifying the presence or absence of a polymorphism in the gene, and comparing the results.

These assays are useful for identifying the genetic markers relating to disease resistance, as discussed above, for identifying other polymorphisms in the gene that may be correlated with other characteristics, and for the general scientific analysis of genotypes and phenotypes.

The genetic markers, methods, and kits of the invention are also useful in a breeding program to improve disease resistance in a breed, line, or population of animals. Continuous selection and breeding of animals that are at least heterozygous and preferably homozygous for a polymorphism associated with a beneficial trait such as disease resistance would lead to a breed, line, or population having higher numbers of offspring in each litter of the females of this breed or line. Thus, the markers are selection tools.

In another embodiment, the invention comprises a method for identifying a genetic marker for disease in a particular animal, species, or population. Male and female animals of the same breed or breed cross or similar genetic lineage are bred, and innate immunity of each pig is determined. A polymorphism in the NRAMP1 gene of each pig is identified and associated with the innate immunity. Preferably, RFLP analysis is used to determine the polymorphism.

In another embodiment, the invention comprises a method for identifying a genetic marker for disease resistance in any particular economic animal other than a pig. Based upon the highly conserved nature of this gene among different animals and the location of the polymorphisms within these highly conserved regions, is it expected that with no more than routine testing as described herein this marker can be applied to different animal species to select for meat quality and/or growth based on the teachings herein. Male and female animals of the same breed or breed cross or similar genetic lineage are bred, and the disease resistance of each animal is determined and correlated. For other animals in which sequences are available a BLAST comparison of sequences may be used to ascertain whether the particular allele is analogous to the one disclosed herein. The analogous polymorphism will be present in other animals and in other closely related genes. The term "analogous polymorphism" shall be a polymorphism which is the same as any of those disclosed herein as determined by BLAST comparisons.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. In this case the Reference NRAMP1 sequence. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73:237–244 (1988); Higgins and Sharp, CABIOS 5:151–153 (1989); Corpet, et al., Nucleic Acids Research 16:10881–90 (1988); Huang, et al., Computer Applications in the Biosciences 8:155–65 (1992), and Pearson, et al., Methods in Molecular Biology 24:307–331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et a., Nucleic Acids Res. 25:3389–3402 (1997). Software for performing BLAST analyses is publicly available, e.g., through the National Center for Biotechnology-Information (www.ncbi.nlm.nih.gov/).

This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873–5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, Comput. Chem., 17:149–163 (1993)) and XNU (Claverie and States, Comput. Chem., 17:191–201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (I) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or preferably at least 70%, 80%, 90%, and most preferably at least 95%.

These programs and algorithms can ascertain the analogy of a particular polymorphism in a target gene to those disclosed herein. It is expected that this polymorphism will exist in other animals and use of the same in other animals than disclosed herein involved no more than routine optimization of parameters using the teachings herein.

It is also possible to establish linkage between specific alleles of alternative DNA markers and alleles of DNA markers known to be associated with a particular gene (e.g. the NRAMP1 gene discussed herein), which have previously been shown to be associated with a particular trait. Thus, in the present situation, taking the NRAMP1 gene, it would be possible, at least in the short term, to select for pigs likely to produce desired meat quality and/or growth, or alternatively against pigs likely to produce less desirable meat quality and/or growth, indirectly, by selecting for certain alleles of a NRAMP1 associated marker through the selection of specific alleles of alternative chromosome markers. As used herein the term "genetic marker" shall include not only the polymorphism disclosed by any means of assaying for the protein changes associated with the polymorphism, be they linked markers, use of microsatellites, or even other means of assaying for the causative protein changes indicated by the marker and the use of the same to influence the meat quality and/or growth of an animal.

As used herein, often the designation of a particular polymorphism is made by the name of a particular restriction enzyme. This is not intended to imply that the only way that the site can be identified is by the use of that restriction enzyme. There are numerous databases and resources available to those of skill in the art to identify other restriction enzymes which can be used to identify a particular polymorphism, for example www.darwin.bio.geneseo.edu which can give restriction enzymes upon analysis of a sequence and the polymorphism to be identified. In fact as disclosed in the teachings herein there are numerous ways of identifying a particular polymorphism or allele with alternate methods which may not even include a restriction enzyme, but which assay for the same genetic or proteomic alternative form.

In yet another embodiment of this invention novel porcine nucleotide sequences have been identified and are disclosed which encode porcine NRAMP1. The cDNA of the porcine NRAMP1 gene as well as some intronic DNA sequences are disclosed. These sequences may be used for the design of primers to assay for the SNP's of the invention or for production of recombinant NRAMP1. The invention is intended to include these sequences as well as all conservatively modified variants thereof as well as those sequences which will hybridize under conditions of high stringency to the sequences disclosed. The term NRAMP1 as used herein shall be interpreted to include these conservatively modified variants as well as those hybridized sequences.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W. H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2× SSC (20× SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1× SSC at 55 to 50° C. Exemplary high stringency conditions include hybridization in 50% formamide, 1 M NaCl, 1% SDS at 37° C., and a wash in 0.1× SSC at 60 to 65° C.

Specificity is typically the function of post-hybridization washes, the critical factors being the ionic strength and temperature of the final wash solution. For DNA-DNA hybrids, the Tm can be approximated from the equation of Meinkoth and Wahl, Anal. Biochem., 138:267–284 (1984): $T_m=81.5°$ C.$+16.6$ (log M)$+0.41$ (% GC)$-0.61$ (% form)$-500/L$; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of the complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the Tm can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology-Hybridization with Nucleic Acids Probes, Part I, Chapter 2, Ausubel, et al., Eds., Greene Publishing and Wiley-Interscience, New York (1995).

The examples and methods herein disclose certain genes which have been identified to have a polymorphism which is associated either positively or negatively with a beneficial trait that will have an effect on disease resistance of that animal. The identification of the existence of a polymorphism within a gene is often made by a single base alternative that results in a restriction site in certain allelic forms. A certain allele, however, as demonstrated and discussed herein, may have a number of base changes associated with it that could be assayed for which are indicative of the same polymorphism. Further, other genetic markers or genes may be linked to the polymorphisms disclosed herein so that assays may involve identification of other genes or gene fragments, but which ultimately rely upon genetic characterization of animals for the same polymorphism. Any assay which sorts and identifies animals based upon the allelic differences disclosed herein are intended to be included within the scope of this invention.

One of skill in the art, once a polymorphism has been identified and a correlation to a particular trait established, will understand that there are many ways to genotype animals for this polymorphism. The design of such alternative tests merely represent optimization of parameters known to those of skill in the art and are intended to be within the scope of this invention as fully described herein.

According to the invention five different marker systems have been identified in the porcine NRAMP1 gene which are associated with innate immunity traits. One polymorphism has been previously disclosed, however, no association with any phenotypic trait has ever been reported; the remaining four are novel polymorphisms. Of the four markers, one is in exon 15, one in the region of exon/intron 2–3, one in the promoter region and one is in intron 1. Novel NRAMP1 sequence has been identified as well as exemplary primers for assaying for the polymorphisms. The markers are associated with innate immunity traits which are non-pathogen specific, so while bacteria is used for challenge it is expected that these traits will improve animal health against a wide variety of diseases or challenges such as stress, viral pathogen, etc. The porcine NRAMP1 cDNA is disclosed in Tuggle et al., "Rapid Communication: Cloning of a Pig Full-Length Natural Resistance Associated Macrophage Protein (NRAMP1) cDNA", J. Anim. Sci. 75:277 (1997). Also disclosed herein are novel primer sequences, however those of skill in the art will readily be able to design a multitude of alternative primers to amplify the region of the polymorphism using the sequence data already known in the art and are available in sources such as Genbank and disclosed herein. A different marker system, using primers that amplify from exon 1–3 and using the HinfI enzyme to detect polymorphic sequences within this region, is disclosed in Sun, H. S., et al., "Mapping of the natural resistance-associated macrophage protein 1 (NRAMP1) gene to pig chromosome 15", Animal Genetics 29:138–140 (1998). Only the polymorphism test (not the specific sequence differences creating the polymorphic restriction fragment length polymorphism), and a method to detect such polymorphisms using HinfI enzyme, were disclosed by Sun et al. Also disclosed herein is an association of genotypes detectable by the HinfI marker with innate immunity traits.

The first marker system is located in the exon/intron 2–3 region and detects 4 alleles produced from A to G or G to A transitions at the positions shown in FIG. 1 (SEQ ID NO:3). For example, using novel primers SEQ ID NO:1 and SEQ ID NO:2 a novel 536 bp sequence, which spans part of intron 2, all of exon 2 and part of intron 3 of the porcine NRAMP1 gene as shown in FIG. 1, can be amplified. FIG. 1 shows the DNA sequence of the 536 bp PCR product (SEQ ID NO:3). The primer regions are shown in bold text, and exon 2 is in italic text. The polymorphic sequences detected with an enzyme like AvaII are underlined while the polymorphic sequences detected with an enzyme like HinfI are double underlined (R=A or G; Y=C or T).

```
PCR Primers
GCGTCAGTCTTCCCTGCTCAG        SEQ ID NO:1

ACGGCAGTTACCACTCTCCATCT      SEQ ID NO:2
```

PCR Conditions

PCR was performed in 10 µl reactions including 1×PCR buffer, 1.5 mM MgCl2, 0.2 mM dNTPs, 3 pmol of each primer and 0.38 U of Taq polymerase.

| PCR program: | | |
|---|---|---|
| 1 x | 95° C. | 2 min, |
| 40 x: | 95° C. | 45 sec |
| | 62° C. | 45 sec |
| | 72° C. | 90 sec |
| 1 x | 72° C. | 5 min |

The A/G transitions can be identified by a restriction enzyme such as Ava II resulting in the following alleles:

| Allele | Position* 72 | Position 364 | Fragments |
|---|---|---|---|
| 1 | G | A | 411, 72, 53 |
| 2 | G | G | 291, 120, 72, 53 |
| 3 | A | A | 483, 53 |
| 4 | A | G | 363, 120, 53 |

*position is calculated based upon 536 bp amplified fragment (SEQ ID NO: 5) All alleles cut at position 53. These alleles can easily be correlated with NRAMP1 sequences disclosed herein and based upon the teachings herein to identify other primers or methods of identification.

By using an enzyme like HinfI and the above 536 bp PCR product, the previously disclosed polymorphism (Sun et al 1998) can also be more easily detected due to the fact that the 536 bp PCR product can amplify this region in a more robust manner with more pig DNA samples than the technology reported in the Sun et al 1998 publication. Below is also disclosed novel sequence differences causing the HinfI RFLP which were not disclosed in the Sun et al 1998 publication.

Thus either the AvaII or the HinfI enzyme can be used for detecting polymorphisms within the 536 bp PCR product.

Alleles Detected by Digestion with an Enzyme Like HinfI

| Allele | Position* 176 | Position 331 | Fragments |
|---|---|---|---|
| A | G | C | 360, 100, 76 |
| B | G | T | 205, 155, 100, 76 |
| C | A | T | 231, 205, 100 |

*position is calculated based upon 536 amplified fragment (SEQ ID NO: 5) All alleles cut at position 100. These alleles can easily be correlated with NRAMP1 sequences disclosed herein and upon the teachings herein to identify other primers or methods of identification.

For the second novel marker system 2 alleles are detected in exon 14–15, again with A⇌G transitions. Allele 4 has an A at position 473 of the 615 bp amplified product (with SEQ ID NOS: 5 and 6 primers) and allele 5 has a G at position 473.

NRAMP1 MspA1I Marker(SEQ ID NO:4)

```
Primers
CATGCTGCTGGTCTGTGCC          (SEQ ID NO:5)

ATTGCAAGATTGGTGTTGTCCC       (SEQ ID NO:6)
```

The sequence of PCR product is shown in FIG. 2, which is DNA sequence of the 615 bp PCR product (SEQ ID NO:4). The primer regions are shown in bold text, the polymorphic MspAI site is underlined and intron 14 is in italic text.

Restriction Fragment Detected with MspA1I

| Fragments | 142bp | (both alleles) |
|---|---|---|
| | 473bp | (allele 4) |
| | 152bp and 321bp | (allele 5) |
| R = A or G | | |

Allele 4=A at position 473; Allele 5=G at position 473.

PCR Conditions

PCR was performed in 15 µl reactions including 1×PCRbuffer, 1.5 mM MgCl2, 0.17 mM dNTPs, 4 pmol of each primer and 1 U of Taq polymerase.

PCR Program:
1×(95° C. 1 min)
31×(95° C. 30 s, 56° C. 1 min, 72° C. 1 min)
1×(72° C. 5 min)

For the third and fourth novel marker systems, two different sets of polymorphisms are found using two different enzymes digesting the same 934 bp PCR product.

In the third marker system, 2 alleles are detected in intron 1, using the SmaI enzyme, again with A⇌G transitions. Allele 6 (determined by SmaI digestion of the PCR product) has a G at position 737 of the 934 bp PCR product, while Allele 7 (determined by SmaI digestion of the PCR product) has an A at position 737.

In the fourth marker system, 2 alleles are detected in the promoter region, using the NlaIII enzyme, again with A⇌G transitions. Allele 8 (determined by NlaIII digestion of the PCR product) has a G at position 310 of the 934 bp PCR product, while Allele 9 (determined by NlaIII digestion of the PCR product) has an A at position 310.

5'UTR NRAMP1 PCR product of 934 bp: (SEQ ID NO:7)
5' UTR NRAMP1 PCR primers:
Forward Primer name: NR1 (SEQ ID NO:8)
5' TGA RCY CTT CAT TTA ACA GAA GA 3'
R=A or G
Y=C or T
Reverse Primer name: NR942 (SEQ ID NO: 9)
5' GGC TCT GAG CAG GGA AGA CT 3'
PCR Conditions
Mg++conc 2.5 mM, dNTPs-conc 200.0 $\mu$M, Taq 0.375U
Cycle profile 94C. for 3 min; 35×[94c for 45 s; 59.3C. for 45 s; 72C. for 1 min] 72C. for 10 min.
PCR-Annotation Amplification was performed using 25 ng of genomic DNA and 0.3 $\mu$M of each primer (10 pmol/ul) in a reaction volume of 10 $\mu$l.

FIG. 3 is the sequence of 934 bp PCR product (amplifies 5'UTR to intron 1):

The two polymorphic sites are underlined (R=A or G). Primer sequences are in bold, with the reverse complement of the 3' primer shown.

SmaI Digestion

Digestion mix: Per sample to be digested, a mix was prepared consisting of 2 ul of 10× J buffer (Promega, Inc), 8 U of SmaI enzyme (Promega, Inc) in a final volume of 14 ul. To each 6 uL PCR product, add 14 uL digestion mix and incubate with oil overnight at room temp. Check digestion pattern on a 2% agarose gel.

Expected Band Sizes:
Allele 6: 505bp, 232bp, 198 bp
Allele 7: 505bp, 430bp

NlaIII Digestion

Digestion mix: Per sample to be digested, a mix was prepared consisting of 1.5 ul of 10×NEB4 buffer (New England Biolabs, Inc.), 6 U of NlaIII enzyme (New England Biolabs, Inc) and 1.5 ug bovine serum albumin in a final volume of 10.5 ul. To each 4.5 uL PCR product, add 10.5 uL digestion mix and incubate with oil overnight at 37 C. Check digestion pattern on a 2% agarose gel.

Expected Band Sizes:
Allele 8: 310 bp, 281 bp, 142 bp, 75 bp, 71 bp, 56 bp
Allele 9: 281 bp, 200 bp, 142 bp, 110 bp, 75 bp, 71 bp, 56 bp

EXAMPLE 1

Bacterial Challenge and Association Testing

Summary

To test the utility of the marker tests to identify animals differing for innate immunity traits, two batches of pigs were experimentally challenged with *Salmonella cholerasuis* and infection related measurements were taken post infection. NRAMP1 polymorphisms were genotyped in the challenged animals. Association analysis revealed statistically significant effects of NRAMP1 genotype on fecal bacteria counts, as well as several measures of immune cell numbers, during the challenge. Controlling fecal bacterial counts has economic value as an infected animal is the main source of transmission of the disease to healthy animals. Thus a marker that would identify animals with decreased fecal bacterial counts would be valuable and have utility.

Pregnant sows were pre-selected based on data from preliminary NRAMP1 genotype analysis and a crude in vitro macrophage bactericidal assay results. From these sows, two separate experiments of 42 piglets (8–19 days old) were derived and piglets shipped to isolation facilities. Piglets consisted of 2 lines of pigs from two different farms. Piglets were determined to be *Salmonella*-free by frequent bacterial culture of fecal material. Piglets were divided into principals and controls and grown to 7–9 weeks of age prior to intranasal challenge with 1 billion colony forming units of *Salmonella choleraesuis* χ3246. The control group (saline inoculated) consisted of 1 piglet/litter (Exp #1, n=13; Exp #2, n=12). The principal group (*Salmonella* infected) consisted of 2 or 3 piglets/litter (Exp #1, n=29; Exp #2, n=30). Following challenge, animals were monitored daily for temperature, clinical signs and *Salmonella* shedding (qualitative and quantitative). Pigs were necropsied post *S. choleraesuis* or saline inoculation and quantitative bacteriology (most probable number) was performed on ileocecal lymph node and from fecal samples at the end of the challenge. Blood samples taken before challenge and at necropsy were used to assess immune cell numbers and response to infection. Portions of mesenteric lymph node, spleen, liver, lung, and muscle were collected and frozen in liquid nitrogen for DNA analysis. Piglets were also genotyped by using several NRAMP1 marker systems described above. Results are shown in Tables 1–5, and genotype frequencies within this challenge population for each of the markers is shown in Table 6.

Statistical Treatment of Data Within Line Analysis

Multiallelic Markers

For markers with more than 2 alleles (NRAMP1-HinfI and NRAMP1-AvaII) the following mixed model was used to estimate the contrast of each allele with all the others combined (1—all, 2—all, etc.). These are therefore individual allele substitution effects. The expected difference between a "1/1" genotype and a "not-1/not-1" genotype is two times the allele substitution effect. General linear models were used:

Trait=sowid+experiment+barn+allele1+allele2+allele3 (+allele 4 for NRAMP1-AvaII).

with sowid as random effect and experiment and barn as fixed effects. Significance p-values for each of the allele substitution effects were recorded from this model.

Bi-allelic Markers

For markers with 2 alleles Least square means (LS means) with standard errors (s.e.) were estimated for the 3 genotype classes from the following model:

Trait=sowid+experiment+barn+genotype with sowid as random effect and experiment and barn as fixed effects. Significant p-values for genotype comparisons were also recorded from this model.

Analysis Across Lines

The same models were used for the across lines analyses as described for the within line analyses with the only difference that a fixed effect for line was added.

Results and Discussion

Overall results are summarized in the following tables. The data were log transformed for the following traits: all bacterial counts as well as macro1, macro2, mono2 and wbc1, because of the non-normal distribution of the data, a widely accepted treatment for non-normally distributed data sets.

As can be seen from the data, NRAMP1 genotypes are associated with differences in fecal bacterial counts (FMPND6; fecal bacterial count on day 6 of challenge), and that this is seen in one or both lines and/or in the combined samples for every marker system. Some alleles are found to be associated with FMPND6 in only one of the analyses, often due to lack of informativeness of the marker.

Also shown by the data are NRAMP1 genotypes that are associated with several innate immune defense measures. These parameters are critical for control of and recovery from infection, and include fever (temperature) and numbers of immune cells (i.e. white blood cells, lymphocytes, neutrophils, monocytes) before and after infection. As above, some alleles are found to be associated with innate immune traits in only one of the analyses, often due to lack of informativeness of the marker.

TABLE 1

NRAMP1 Hinf1 genotype association analysis in example 1.

| | Allele substitution effects Line B | | | | | |
|---|---|---|---|---|---|---|
| | 1-all | | 2-all | | 3-all | |
| TRAIT[a] | Effect | P value | Effect | P value | Effect | P value |
| TempD0 | 0.03 | 0.81 | −0.04 | 0.63 | 0.01 | 0.96 |
| TempD1 | −0.13 | 0.47 | 0.22 | 0.06 | −0.09 | 0.61 |
| TempD2 | −0.31 | 0.19 | 0.11 | 0.47 | 0.20 | 0.39 |
| TempD3 | −0.18 | 0.42 | −0.27 | 0.05 | 0.45 | 0.04 |
| TempD4 | 0.24 | 0.29 | −0.18 | 0.23 | −0.07 | 0.77 |
| TempD6 | −0.40 | 0.07 | 0.16 | 0.27 | 0.24 | 0.27 |
| TempD7 | −0.43 | 0.06 | 0.22 | 0.13 | 0.21 | 0.34 |
| FMPND6 | 0.81 | 0.17 | 0.27 | 0.43 | −1.09 | 0.06 |
| lymph_diff | 1.77 | 0.06 | −0.60 | 0.30 | −1.16 | 0.18 |
| pneut2 | 3.48 | 0.52 | −6.31 | 0.08 | 2.83 | 0.62 |

[a]Traits are:
TEMPD0 = temperature on day 0 of challenge,
TEMPD1 - temperature on day 1 after challenge, etc.;
FMPND6 = mean fecal Salmonella count on day 6 after challenge;
lymph_diff = difference in blood lymphocyte numbers between days 0 and 7 after challenge;
pneut2 = percentage of blood neutrophils after challenge.

TABLE 2a

NRAMP1 Ava11 genotype association analysis in example 1.

| | Allele substitution effects (p value) | | | | | | | |
|---|---|---|---|---|---|---|---|---|
| | LineA | | | | Line B | | | |
| TRAIT[a] | 1-all | 2-all | 3-all | 4-all | 1-all | 2-all | 3-all | 4-all |
| TempD0 | .04 (.77) | −.10 (.64) | −.86 (.13) | .92 (.11) | .05 (.55) | .03 (.69) | −.08 (.34) | — |
| TempD1 | −.06 (.59) | −.02 (.88) | −.33 (.43) | .41 (.30) | .25 (.02) | −.08 (.41) | −.17 (.10) | — |
| TempD2 | −.01 (.96) | −.07 (.79) | −.42 (.69) | .50 (.58) | .06 (.71) | −.10 (.50) | .04 (.82) | — |
| TempD3 | .25 (.31) | −.06 (.81) | .10 (.91) | −.30 (.72) | .13 (.28) | .17 (.11) | −.30 (.02) | — |
| TempD4 | −.22 (.47) | −.52 (.27) | — | .74 (.29) | −.15 (.33) | .005 (.97) | .14 (.34) | — |
| TempD6 | −.001 (.74) | .002 (.59) | −.002 (.83) | .001 (.91) | 0 (.63) | 0 (.98) | 0 (.64) | — |
| TempD7 | −.29 (.21) | .48 (.07) | .46 (.59) | −.65 (.40) | .18 (.33) | −.004 (.98) | −.17 (.34) | — |
| FMPND1 | −1.4 (.04) | −.44 (.30) | 4.1 (.03) | −2.2 (.13) | −.22 (.51) | .11 (.66) | .11 (.67) | — |
| FMPND6 | −.33 (.64) | −.69 (.48) | −.59 (.81) | 1.6 (.51) | −.47 (.08) | −.10 (.69) | .56 (.02) | — |
| Macro1 | .11 (.34) | .27 (.07) | −.64 (.22) | .25 (.53) | .03 (.59) | .04 (.34) | −.06 (.17) | — |
| Macro2 | .03 (.75) | −.08 (.49) | −.38 (.38) | .42 (.28) | .01 (.86) | .13 (.09) | −.14 (.07) | — |
| Macro_diff | −.15 (.78) | −1.04 (.13) | .79 (.73) | .40 (.83) | .09 (.76) | .24 (.37) | −.33 (.27) | — |
| neut1 | .53 (.48) | −.26 (.81) | −2.25 (.40) | 1.97 (.44) | −.43 (.51) | .66 (.57) | −.22 (.64) | — |
| neut2 | .08 (.97) | .07 (.98) | 3.58 (.64) | −3.73 (.62) | .10 (.90) | 1.78 (.01) | −1.88 (.02) | — |
| neut_diff | −.77 (.61) | −.01 (.99) | 6.65 (.24) | −5.87 (.31) | .53 (.55) | 1.12 (.16) | −1.65 (.07) | — |
| lymph1 | .73 (.36) | −5.23 (.03) | .26 (.92) | 4.25 (.20) | 2.09 (.03) | −1.12 (.18) | −.97 (.29) | — |
| lymph2 | .89 (.50) | −.77 (.55) | −1.45 (.78) | 1.33 (.77) | −.32 (.69) | −.93 (.20) | 1.25 (.12) | — |
| lymph_diff | 1.51 (.46) | −.88 (.69) | −3.87 (.60) | 3.23 (.63) | −2.20 (.02) | .01 (.99) | 2.19 (.02) | — |
| pneut1 | −3.37 (.06) | 8.09 (.05) | −4.49 (.36) | −.22 (.97) | −4.87 (.17) | 4.11 (.20) | .76 (.82) | — |
| pneut2 | — | — | — | — | 1.56 (.69) | 5.44 (.16) | −7.00 (.07) | — |
| pneut_diff | — | — | — | — | 8.57 (.10) | −2.10 (.64) | −6.47 (.20) | — |
| Plymph1 | 1.68 (.18) | −14.4 (.005) | 3.03 (.44) | 9.65 (.08) | 6.45 (.08) | −4.69 (.14) | −1.76 (.61) | — |

TABLE 2a-continued

NRAMP1 Ava11 genotype association
analysis in example 1.

Allele substitution effects (p value)

| | Line A | | | | Line B | | | |
|---|---|---|---|---|---|---|---|---|
| TRAIT[a] | 1-all | 2-all | 3-all | 4-all | 1-all | 2-all | 3-all | 4-all |
| Plymph2 | — | — | — | — | −4.19 (.36) | −5.17 (.23) | 9.36 (.05) | — |
| Plymph_d | — | — | — | — | −11.0 (.03) | 1.8 (.67) | 9.19 (.07) | — |

[a]Traits are:
TEMPD0 = temperature on day 0 of challenge,
TEMPD1 - temperature on day 1 after challenge, etc.;
FMPND6 = mean fecal Salmonella count on day 6 after challenge;
Macro1 and 2 = macrophage numbers before (1) and after (2) challenge;
Macro_diff = difference in macrophage numbers before and after challenge;
lymph 1, 2, diff = lymphocyte numbers before (1) and after (2) challenge and the difference between these values;
pneut1, 2, diff = percentage of neutrophils before (1) and after (2) challenge and the difference between these values;
plymph 1, 2, diff = percentage of lymphocytes before (1) and after (2) challenge and the difference between these values.

TABLE 2b

NRAMP1 Avall genotype association analysis
(lines combined) in example 1.

Allele substitution effects (p-value)
Lines A and B combined

| TRAIT[a] | 1-all | 2-all | 3-all | 4-all |
|---|---|---|---|---|
| FMPND6 | −.56 (.06) | −.51 (.19) | .14 (.73) | .92 (.28) |

[a]FMPND6 = mean fecal Salmonella count on day 6 after challenge

TABLE 3

NRAMP1 Smal genotype association
analysis in example 1.

| | Line A | | | | Line B | | | |
|---|---|---|---|---|---|---|---|---|
| | LSmeans (s.e.) | | | | LSmeans (s.e.) | | | |
| TRAIT[a] | 66 | 67 | 77 | P | 66 | 67 | 77 | p |
| FMPND6 | .70 (.91) | 1.15 (1.0) | .41 (2.1) | 0.85 | .14 (.25) | −1.02 (.45) | — | 0.04 |

[a]FMPND6 = mean fecal Salmonella count on day 6 after challenge

TABLE 4

NRAMP1 NIalll genotype association analysis
(lines combined) in example 1.

Line A and B combined
LSmeans (s.e.)

| TRAIT[a] | 88 | 89 | 99 | p |
|---|---|---|---|---|
| FMPND6 | 1.19 (0.15) | 2.27 (0.45) | — | .0006 |

[a]FMPND6 = mean fecal Salmonella count on day 6 after challenge

TABLE 5

NRAMP1 MspAl genotype association analysis in example 1.

| | Line A | | | | Line B | | | |
|---|---|---|---|---|---|---|---|---|
| | LSmeans (s.e.) | | | | LSmeans (s.e.) | | | |
| TRAIT[a] | 44 | 45 | 55 | p | 44 | 45 | 55 | p |
| FMPND6 | −.11 (1.3) | 1.3 (1.0) | 1.2 (.90) | 0.71 | −.46 (.86) | −.87 (.36) | .24 (.23) | 0.06 |

[a]FMPND6 = mean fecal Salmonella count on day 6 after challenge

TABLE 6

Genotype frequencies within challenge population.

| | | 11 | 12 | 13 | 22 | 23 | 33 | | | |
|---|---|---|---|---|---|---|---|---|---|---|
| NRAMP1-Hinfl | Line A | — | — | — | 9 | 5 | 1 | | | |
| | Line B | — | 8 | 2 | 29 | 5 | — | | | |

| | | 11 | 12 | 13 | 14 | 22 | 23 | 24 | 33 | 34 | 44 |
|---|---|---|---|---|---|---|---|---|---|---|---|
| NRAMP1-Avail | Line A | 5 | 6 | — | — | 2 | — | 1 | — | 1 | — |
| | Line B | 4 | 13 | 14 | — | 5 | 5 | — | 3 | — | — |

| | | 66 | 67 | 77 |
|---|---|---|---|---|
| NRAMP1-Smal | Line A | 9 | 4 | 2 |
| | Line B | 37 | 7 | — |

| | | 88 | 89 | 99 |
|---|---|---|---|---|
| NRAMP1-NIalll | Line A | 10 | 5 | — |
| | Line B | 42 | — | — |

| | | 44 | 45 | 55 |
|---|---|---|---|---|
| NRAMP1-MspA1 | Line A | 4 | 5 | 6 |
| | Line B | 2 | 10 | 32 |

EXAMPLE 2

Bacterial Challenge and Association Testing

Summary

To further assess the utility of the marker tests to identify animals that differ in innate disease resistance, some of these markers were tested on offspring of sires that were susceptible or resistant to Salmonellosis. The offspring were challenged orally with S. choleraesuis and infection and innate immunity related traits were measured. Association analyses revealed that potential effects of NRAMP1 genotype on fever, bacterial load in liver and spleen, and immune cell numbers and function. The presence of bacteria in internal organs demonstrates that the animal's immune system was unable to control spread of the infection. Reduced bacterial counts and lower fever in one genotype class are indicative of the heightened ability of those animals to control infection. These traits have economic value since fever and systemic infection decrease appetite and suppress growth and perfomance in a measurable way.

Experiment Description

Challenged pigs were offspring of a reference population that was bred from sires was that differed in susceptibility to Salmonellosis. The founder sires (commercial line Y) were selected based on the results of a preliminary study to identify individuals that differed in susceptibility to infection with S. choleraesuis. Sires were mated to 23 F1 gilts (crosses of commercial lines Y×Z and Z×Y) and produced one litter. Three to nine piglets from each litter were selected for oral challenge with $8 \times 10^8$ S. choleraesuis (n=216). Piglets were challenged at 6 weeks of age. Blood samples were taken from animals for innate immunity studies one week before challenge, on the day of challenge and at necropsy. Traits of innate immunity included total leukocyte count and differential, bacterial uptake, phagocytosis and killing by neutrophils, lymphocyte proliferation against several antigens (Table Ex2–4). One week after challenge, animals were necropsied and the amount of Salmonella in liver and spleen was determined by quantitative culture on one gram of tissue.

DNA was also isolated from blood for genetic analysis. Pigs were genotyped by using several NRAMP1 marker systems described above; genotype frequencies are shown in Table Ex2-1. Statistical associations between genotypes and measured traits are shown in Table Ex2-2 and Ex2-3.

Statistical Treatment of Data

The associations between the sequence polymorphisms and phenotypes were tested using mixed model procedures (SAS™ procedure MIXED) with a model which always included dam as a random effect and Group and marker parameters as fixed effects. Single point significance values are reported, without making adjustments for multiple comparisons.

Multiallelic Markers

For our markers with more than 2 alleles (NrampAva-II in this population) the following mixed model was used to estimate allele substitution effects, where sowid was random and the other effects are fixed Trait=sowid+group+allele1+allele2+allele3.

Each allele was put in the model as a fixed effect with 3 levels (−1,0 and 1). For allele "1" these values would be −1 for a "not-1/not-1" genotype, 0 for a "1/not-1" genotype and 1 for a "1/1" genotype. Allele substitution effects were estimated and presented with allele 3 arbitrarily set to zero.

Bi-allelic Markers

For our markers with 2 alleles (NrampHinfI in this population) the following mixed model was used to estimate Least square means (Ls means) for the 3 genotype classes, with sowid as random effect and group and genotype as fixed effects.

Trait=sowid+group+genotype

Results and Discussion

Overall results are summarized in the following tables (Tables Ex2-2 and Ex2-3; trait descriptions are in Table Ex2-4). The bacterial count data (SpleenC and LiverC) was log transformed because of the non-normal distribution of the data, a widely accepted treatment for non-normally distributed data sets.

As can be seen from the data in Example 2, NRAMP1 AvaII and HinfI genotypes are associated with differences in the level of bacterial infection and clearance, as noted from statistically significant association with spleen and liver counts; with several traits measuring phagocytic activity; and with the level of fever associated with infection. In addition, white blood cell count before or after infection were associated with NRAMP1 genotypes. These cells are critical for controlling and recovering from infection. The number of white blood cells and their ability to respond to infection.

Some alleles are found to be associated with traits in only one of the analyses, often due to lack of informativeness of the marker. All comparisons are shown for trait and marker systems where sufficiently informative markers for statistical analysis were available.

TABLE Ex2-1

Genotype frequencies within example 2 population.

| NRAMP1-<br>AvaII | genotype | 11 | 12 | 13 | 22 | 23 | 33 | total |
|---|---|---|---|---|---|---|---|---|
| | number | 17 | 45 | 63 | 15 | 21 | 17 | 178* |
| | percentage | 10 | 25 | 35 | 8 | 12 | 10 | 100 |

| NRAMP1-<br>HinfI | genotype | 11 | 12 | 22 | total |
|---|---|---|---|---|---|
| | number | 15 | 66 | 95 | 176* |
| | percentage | 9 | 37 | 54 | 100 |

*not all animals genotyped for HinfI

TABLE Ex2-2

Nramp1 AvaII genotype association analysis in example 2

| | | | Allele substitution effect* | | | contrast p-values | | |
|---|---|---|---|---|---|---|---|---|
| Trait | mean (s.e) | s.d. | 1 | 2 | 3 | 1 vs 2 | 1 vs 3 | 2 vs 3 |
| SpleenC | 1.16 (0.09) | 1.25 | 0.59 | 0.09 | 0 | 0.007 | 0.0012 | 0.56 |
| liverC | 2.16 (0.11) | 1.45 | 0.65 | −0.02 | 0 | 0.0006 | 0.0006 | 0.91 |
| wbc1 | 6.63 (0.30) | 3.91 | −0.36 | −0.23 | 0 | 0.75 | 0.39 | 0.45 |
| wbc2 | 7.23 (0.23) | 3.01 | −0.68 | −0.94 | 0 | 0.49 | 0.08 | 0.009 |
| wbc3 | 10.53 (0.34) | 4.1 | −0.54 | 0.87 | 0 | 0.04 | 0.45 | 0.17 |
| wbc_d12 | 0.57 (0.34) | 4.46 | −0.08 | −0.84 | 0 | 0.19 | 0.90 | 0.07 |
| wbc_d23 | 3.14 (0.38) | 4.58 | 0.02 | 1.67 | 0 | 0.03 | 0.98 | 0.02 |
| wbc_d13 | 3.56 (0.40) | 4.79 | −0.52 | 0.86 | 0 | 0.08 | 0.53 | 0.21 |
| mon1 | 2.94 (0.19) | 2.47 | −0.26 | −0.70 | 0 | 0.21 | 0.48 | 0.04 |
| mon2 | 2.40 (0.14) | 1.88 | 0.23 | −0.07 | 0 | 0.31 | 0.45 | 0.79 |
| mon3 | 3.54 (0.24) | 2.83 | −0.31 | −0.24 | 0 | 0.88 | 0.53 | 0.58 |
| mon_d12 | −0.54 (0.21) | 2.81 | 0.55 | 0.68 | 0 | 0.77 | 0.22 | 0.10 |
| SICA_pre | 222.4 (19.2) | 253 | 81.10 | 0.73 | 0 | 0.05 | 0.05 | 0.98 |
| SICA_pos | 68.01 (8.64) | 103 | 13.09 | −17.57 | 0 | 0.10 | 0.50 | 0.33 |
| CA_LPSpr | 44.93 (3.91) | 51.3 | 9.95 | −6.05 | 0 | 0.06 | 0.25 | 0.40 |
| CA_LPSpo | 16.99 (3.06) | 36.6 | 0.70 | −6.71 | 0 | 0.26 | 0.92 | 0.29 |
| uptake | 0.54 (0.11) | 1.41 | −0.07 | 0.29 | 0 | 0.09 | 0.74 | 0.11 |
| killing | 83.48 (1.57) | 20.6 | −6.54 | 1.63 | 0 | 0.01 | 0.05 | 0.59 |
| phagoc | 3.38 (0.56) | 7.3 | −0.83 | 0.91 | 0 | 0.03 | 0.32 | 0.18 |
| perc_pmn | 73.63 (1.19) | 15.6 | −1.99 | −6.89 | 0 | 0.04 | 0.42 | 0.003 |
| t1 | 39.48 (0.04) | 0.35 | 0.06 | 0.03 | 0 | 0.69 | 0.35 | 0.64 |
| t2 | 39.55 (0.04) | 0.34 | 0.12 | 0.04 | 0 | 0.29 | 0.08 | 0.54 |
| t3 | 38.91 (0.03) | 0.27 | 0.02 | 0.07 | 0 | 0.36 | 0.76 | 0.23 |
| t4 | 39.58 (0.04) | 0.33 | 0.03 | 0.04 | 0 | 0.92 | 0.68 | 0.62 |
| t5 | 39.64 (0.05) | 0.49 | −0.02 | −0.04 | 0 | 0.85 | 0.86 | 0.72 |
| t6 | 40.83 (0.09) | 0.82 | −0.31 | −0.19 | 0 | 0.53 | 0.07 | 0.30 |
| t7 | 41.51 (0.04) | 0.38 | −0.06 | −0.10 | 0 | 0.71 | 0.46 | 0.27 |
| t8 | 41.37 (0.04) | 0.35 | 0.24 | 0.06 | 0 | 0.02 | 0.0007 | 0.42 |
| t9 | 40.90 (0.06) | 0.52 | 0.07 | −0.09 | 0 | 0.21 | 0.56 | 0.39 |
| t10 | 40.80 (0.06) | 0.57 | 0.08 | −0.26 | 0 | 0.01 | 0.49 | 0.03 |
| t11 | 40.30 (0.08) | 0.68 | 0.16 | −0.14 | 0 | 0.07 | 0.28 | 0.36 |
| t12 | 40.40 (0.06) | 0.57 | −0.03 | −0.02 | 0 | 0.97 | 0.82 | 0.84 |

*Allele 3 set to zero for these comparisons

TABLE Ex2-3

Nrampl Hinfl genotype association analysis in example 2

| Trait | LSmeans (s.e.) 11 | 12 | 22 |
|---|---|---|---|
| SpleenC | 0.77 (0.32) a | 1.29 (0.16) b | 1.20 (0.14) b |
| liverC | 1.64 (0.33) e c | 2.33 (0.17) f | 2.29 (0.15) d |
| wbc1 | 6.80 (0.63) a | 6.11 (0.36) b | 6.59 (0.34) a |
| wbc2 | 6.51 (0.67) a | 6.67 (0.32) e | 7.53 (0.27) b f |
| wbc3 | 12.18 (1.11) a c | 10.74 (0.61) b | 9.81 (0.48) a d |
| wbc_d12 | −0.73 (0.90) a c | 0.49 (0.49) b | 1.12 (0.45) a d |
| wbc_d23 | 5.91 (1.24) a e | 3.89 (0.69) b c | 2.40 (0.52) f d |
| wbc_d13 | 4.99 (1.22) a | 4.36 (0.69) a | 3.10 (0.56) b |
| mon1 | 2.16 (0.62) a | 2.43 (0.29) c | 3.14 (0.25) b d |
| mon2 | 2.23 (0.50) | 2.17 (0.25) | 2.43 (0.22) |
| mon3 | 3.77 (0.78) | 3.19 (0.42) | 3.59 (0.34) |
| mon_d12 | 0.10 (0.77) | −0.30 (0.36) | −0.75 (0.31) |
| SICA_pre | 178.3 (69.1) | 212.6 (33.0) | 244.2 (28.7) |
| SICA_pos | 17.57 (31.9) a c | 67.43 (16.5) b | 79.67 (13.4) d |
| CA_LPSpr | 39.69 (13.8) | 37.82 (6.95) c | 52.59 (6.08) d |
| CA_LPSpo | 3.57 (11.3) a | 16.26 (5.81) | 20.86 (4.69) b |
| uptake | 0.88 (0.35) a | 0.66 (0.17) c | 0.30 (0.15) b d |
| killing | 84.37 (5.83) | 86.78 (2.84) c | 79.74 (2.48) d |
| phagoc | 5.67 (1.31) c e | 3.19 (0.68) d | 2.53 (0.61) f |
| perc_pmn | 67.31 (4.21) e | 70.87 (1.96) g | 77.92 (1.68) f h |
| t1 | 39.28 (0.18) a | 39.57 (0.07) a,b | 39.48 (0.04) b |
| t2 | 39.46 (0.18) | 39.62 (0.08) | 39.56 (0.05) |
| t3 | 39.01 (0.15) | 38.97 (0.06) a | 38.90 (0.03) b |
| t4 | 39.54 (0.19) | 39.62 (0.08) | 39.57 (0.04) |
| t5 | 39.49 (0.28) | 39.65 (0.11) | 39.65 (0.06) |
| t6 | 40.40 (0.48) | 40.90 (0.19) | 40.82 (0.11) |
| t7 | 41.64 (0.22) a | 41.36 (0.09) b c | 41.54 (0.05) d |
| t8 | 41.50 (0.21) | 41.40 (0.09) | 41.37 (0.06) |
| t9 | 40.78 (0.27) | 40.84 (0.13) | 40.96 (0.10) |
| t10 | 40.53 (0.35) a | 40.58 (0.13) e | 40.90 (0.09) b f |
| t11 | 39.91 (0.39) a | 40.18 (0.17) | 40.34 (0.11) b |
| t12 | 40.35 (0.31) | 40.44 (0.14) | 40.44 (0.09) |

LSmeans significance levels between genotypes with different subscripts:

| a–b | p < .3 | i–j | p < .005 |
|---|---|---|---|
| c–d | p < .1 | k–l | p < .001 |
| e–f | p < .05 | m–n | p < .0005 |
| g–h | p < .01 | o–p | p < .0001 |

TABLE Ex2-4

| Trait Code | Trait description |
|---|---|
| CA/LPS1 | Stimulation index in presence of Concavalin A + SCS A50 LPS on day 29 |
| CA/LPS2 | Stimulation index in presence of Concavalin A + SCS A50 LPS on day 38 |
| killing | Salmonella killing efficiency of PMNs |
| LiverC | Bacterial counts in liver at one week |
| Lymfo1 | percentage lymphocytes on day 15 |
| Lymfo2 | percentage lymphocytes on day 29 |
| Lymfo3 | percentage lymphocytes on day 38 or post mortem |
| Mono1 | percentage monocytes on day 15 |
| Mono2 | percentage monocytes on day 29 |
| Mono3 | percentage monocytes on day 38 or post mortem |
| mono_d12 | absolute value of mono1-mono2 |
| mono_d23 | absolute value of mono2-mono3 |
| mono_d13 | absolute value of mono1-mono1 |
| Neutro1 | percentage neutrophils on day 15 |
| Neutro2 | percentage neutrophils on day 29 |
| Neutro3 | percentage neutrophils on day 38 or post mortem |
| Pcv1 | packed cell volume on day 15 |
| Pcv2 | packed cell volume on day 29 |
| Pcv3 | packed cell volume on day 38 or post mortem date |
| perc_pmn | percentage PMN's |
| phag | phagocytosis efficiency of PMN's |
| SICA_pos | Stimulation index in presence of Concavalin A on day 38 |
| SICA_pre | Stimulation index in presence of Concavalin A on day 29 |
| SpleenC | Bacterial counts in spleen at one week |
| uptake | Salmonella uptake efficiency of PMN's |
| Wbc1 | White blood cell count on day 15 |
| Wbc2 | White blood cell count on day 29 |
| Wbc3 | White blood cell count on day 38 or post mortem. |
| wbc_d12 | absolute value of wbc1-wbc2 |
| wbc_d23 | absolute value of wbc2-wbc3 |
| wbc_d13 | absolute value of wbc1-wbc3 |

References

Archibald, A., et al., "The PigMaP Consortium Linkage Map of the Pig (Sus scrofa)", Mamm. Genome 6:157–175 (1995)

Green, P., et al., "Documentation for CRI-MAP, version 2.4", Washington University School of Medicine, St. Louis, Mo. (1990)

Hu, J., et al., "Resistance to salmonellosis in the chicken is linked to NRAMP1 and TNC", Genome Res. 7:693–704 (1997)

Malo, D., et al., "Haplotype mapping and sequence analysis of the mouse NRAMP1 gene predict susceptibility to infection with intracellular parasites", Genomics 23:51–61 (1994)

Sun, H. S., et al., "Mapping of the natural resistance-associated macrophage protein 1 (NRAMP1) gene to pig chromosome 15", Animal Genetics 29:138–140 (1998)

Super, M., et al., "Association of low levels of mannan-binding protein with a common defect of opsonisation", Lancet. 25:1236–1239 (1989)

Overall Summary

In both Examples, NRAMP1 genotypes are associated with specific measures of innate disease resistance and disease susceptibility such as fever, systemic infection and immune function. Thus this information and marker systems to determine NRAMP1 genotypes can be used to improve animal health and performance due to the ability to decrease incidence of disease through identifying susceptible animals before they can become sick. Alternatively, the same technologies described above can be used to identify those animals most likely to be the healthiest within a group. Improving these traits have economic value since fever and systemic infection decrease appetite and suppress growth and perfomance.

What is claimed is:

1. A method of screening pigs to determine those more likely to exhibit a biological difference in disease resistance or innate immunity traits comprising:
   obtaining a sample of genetic material from said pig; and
   assaying for the presence of a genotype in said pig which is associated with a biological difference in disease resistance or innate immunity, said genotype characterized by the following:
      a) a polymorphism in the intron2/exon2 of the NRAMP1 gene.

2. The method of claim 1 wherein said polymorphism is located in a region of the NRAMP1 gene selected from the group consisting of: exon 15, intron 2/exon 2, the promoter region, and intron 1 or their equivalents as determined by a BLAST comparison.

3. The method of claim 1 wherein said polymorphism is identifiable by an Ava II restriction enzyme.

4. The method of claim 1 wherein said genotype is a Ava II polymorphism in intron 2/axon 2 of the NRAMP1 gene.

5. The method of claim 1 wherein said polymorphism results in an A⇌G transition in intron 2/exon 2 or its equivalent as determined by a BLAST comparison of SEQ ID NO:3.

6. The method of claim 1 wherein said step of assaying is selected from the group consisting of: restriction fragment length polymorphism (RFLP) analysis, minisequencing, MALD-TOF, SINE, heteroduplex analysis, single strand conformational polymorphism (SSCP), denaturing gradient gel electrophoresis (DGGE) and temperature gradient gel electrophoresis (TGGE).

7. The method of claim 1 further comprising the step of amplifying a region of intron2/exon2 of the NRAMP1 gene or a portion thereof which contains said polymorphism.

8. The method of claim 7 wherein said amplification includes the stops of:
   selecting a forward and a reverse sequence primer capable of amplifying said region of intron2/exon2 of the NRAMP1 gene which contains a polymorphic site.

9. The method of claim 8 wherein said forward and reverse primers are selected from SEQ ID NOS: 1 and 2.

10. The method of claim 7 wherein said amplification includes the steps of:
    selecting a forward and a reverse sequence primer capable of amplifying a region of the NRAMP1 gene which contains a polymorphic Ava II.

11. The method of claim 10 wherein said forward and reverse primers are selected from and based upon primer SEQ ID NO:1 and primer SEQ ID NO:2.

12. A method of screening pigs to determine those more likely to exhibit a biological difference in disease resistance or innate immunity traits comprising:
    obtaining a biological sample of material from said pig; and
    assaying for the presence of a genotype in said pig which is associated with a biological difference in disease resistance or innate immunity traits said genotype characterized by the following:
       a) a polymorphism in intron2/exon2 of the NRAMP1 gene, said polymorphism resulting in and characterized by a nucleotide at a position in intron2/exon2 of SEQ ID NO:3.

13. The method of claim 12 wherein said polymorphism results in an Ava II polymorphic restriction site.

14. A method for screening pigs to determine those with biologically different disease resistance or innate immunity traits, which method comprises of the steps:
    determining the alleles in intron2/exon2 of SEQ ID NO:3 of NRAMP1 present in a pig, said alleles having a polymorphic Ava II site in the NRAMP1 gene;
    determining the alleles of other markers for genes known to affect innate immunity; and
    selecting for a pig with a favorable combination of alleles associated with improved resistance to pathogenic infection observed when a favorable combination of alleles are present and against those not able to stave off infection when the favorable combination of alleles is not present.

15. The method of claim 14 wherein the determination of NRAMP1 alleles comprises determining the presence of at least one allele associated with at least one DNA marker linked either directly or indirectly to NRAMP1.

16. The method as claimed in claim 14 wherein the DNA marker is a microsatellite.

17. A method of identifying the presence or absence of an allele associated with a biological difference in disease resistance or innate immunity in a pig comprising:
    analyzing intron2/exon2 of SEQ ID NO:3 in the NRAMP1 gene encoding sequence present in said pig;
    comparing said sequence with the sequence of NRAMP1 alleles known to be associated with a biological difference in disease resistance or innate immunity and
    correlating said allele with the trait of a biological difference in disease resistance or innate immunity in a pig, a group or a population of pigs.

18. A method of screening pigs to determine those more likely to have biologically different general health traits comprising:
    obtaining a sample of genetic material from said pig; and
    assaying for the presence of a genotype in said pig which is associated with biologically different improved general health traits, said genotype characterized by the following:
       a) a polymorphism in intron2/exon2 of SEQ ID NO:3 in the NRAMP1 gene.

19. The method of claim 18 wherein said polymorphism is identifiable by an Ava II restriction enzyme.

20. The method of claim 18 wherein said genotype is a Ava II polymorphism in intron 2/exon 2 of the NRAMP1 gene.

21. The method of claim 18 wherein said polymorphism results in an A⇌G transition in intron 2/exon 2 or its equivalent as determined by a BLAST comparison of SEQ ID NO:3.

22. The method of claim 18 wherein said step of assaying is selected from the group consisting of: restriction fragment length polymorphism (RFLP) analysis, minisequencing, MALD-TOF, SINE, heteroduplex analysis, single strand conformational polymorphism (SSCP), denaturing gradient gel electrophoresis (DGGE) and temperature gradient gel electrophoresis (TGGE).

23. The method of claim 18 further comprising the step of amplifying region of intron2/exon2-of said NRAMP1 gene or a portion thereof which contains said polymorphism.

24. The method of claim 23 wherein said amplification includes the steps of:
    selecting a forward and a reverse sequence primer capable of amplifying said region of intron2/exon2 in the NRAMP1 gene which contains a polymorphic site.

25. The method of claim 24 wherein said forward and reverse primers are selected from SEQ ID NOS: 1 and 2.

26. The method of claim 23 wherein said amplification includes the steps of:
   selecting a forward and a reverse sequence primer capable of amplifying said region of the NRAMP1 gene which contains a polymorphic Ava II.

27. The method of claim 26 wherein said forward and reverse primers are selected from and based upon primer SEQ ID NO:1 and primer SEQ ID NO:2.

* * * * *

SEQUENCE LISTING

<160> NUMBER OF SEQ ID NOS: 9

<210> SEQ ID NO 1
<211> LENGTH: 21

```
<212> TYPE: DNA
<213> ORGANISM: Sus scrofa

<400> SEQUENCE: 1
gcgtcagtct ccctgctca g                                              21

<210> SEQ ID NO 2
<211> LENGTH: 23
<212> TYPE: DNA
<213> ORGANISM: Sus scrofa

<400> SEQUENCE: 2
acggcagtta ccactctcca tct                                           23

<210> SEQ ID NO 3
<211> LENGTH: 536
<212> TYPE: DNA
<213> ORGANISM: Susscrofa

<400> SEQUENCE: 3
gcgtcagtct ccctgctca gagcccatgc cctctccaca tcctctgtgg caagaggcca    60
tcaggatctg grgacctctg cattcacatg gaaggagagg aatccagaag gctctgcttc  120
tcacacatct tctggaaggt ctggtcgagg gatggatgtg atggactgaa gaaagraatc  180
aagggctcct attcagctgg ggcttcattt gctttcgccc tgccaccaga acaggcagg   240 tcactcacca aggctcttgg ggcccctggc aggtgacaca ggccccccaa agcagagcag  300
aacccaatat ggctccatct ccagctcacc gagyccaggg ccaccacaag tacctcccgg  360
aggracctac ctgagtgaga agatccccat cccgaatgca gaaccggtga gaatgctgga  420
aacttcctgg ggtcttttag gatggatagg atcccatggg atctctctgg ccaagggagg  480
gaggtccccc gaagaccagg gcaagtccct tccagatgga gagtggtaac tgccgt      536

<210> SEQ ID NO 4
<211> LENGTH: 615
<212> TYPE: DNA
<213> ORGANISM: Sus scrofa

<400> SEQUENCE: 4
catgctgctg gtctgtgcca tcaacttta ctttctggtc agctacctgc ccagcctccc    60 ccacccgcc tacttcggcc ttgtagcact actggctgtc atctacctgg gcctcaccac   120
ctacctggta ccgtagtgtc agcgggtgcc ttggggatgg gggcagcacg gaggggagac  180
catagatgga gggctgggga gggggatac actggggctt ccccaaaggt cttgttctct   240 cccttctca tggtcgcctc tcccccaggt ctggacctgt cttatcgccc atggagctac   300
ccttctggtc cacagttccc atcaacactt tctgtatggg cttctggaat aggagcagga  360
gaaggaaaag acctcgggat gagctaccct gcagggcttg gctgagggtg gaatgcgtgg  420
ggcatattgg cctgctggac aggtgggcat ggcggggggac ccrctgtgtg gaagcagcta  480
gatggagcgc aagtttttgg aagcaggcca acctgagttc cttagggacc tgcagtttcc  540
taacttggac aagttactca acctctggat ctcagtgtct tcatctataa aatgggacaa  600
caccaatctt gcaat                                                   615

<210> SEQ ID NO 5
<211> LENGTH: 19
<212> TYPE: DNA
<213> ORGANISM: Sus scrofa
```

```
<400> SEQUENCE: 5
catgctgctg gtctgtgcc                                                19

<210> SEQ ID NO 6
<211> LENGTH: 22
<212> TYPE: DNA
<213> ORGANISM: Sus scrofa

<400> SEQUENCE: 6
attgcaagat tggtgttgtc cc                                            22

<210> SEQ ID NO 7
<211> LENGTH: 934
<212> TYPE: DNA
<213> ORGANISM: Sus scrofa

<400> SEQUENCE: 7
tgagcccttc atttaacaga agaaataagc tcagaggcag gacaggatct ggtgacaacg    60
tcaaatggat ccatggtaga agcaagacca gaattccagg accctcttct tcagaggacc   120
tccttagcct ggaacttcaa tgcatgtccc cgtggccggg cttggaaggt cttttccttt   180
gtggcactcc taggtggtca tggggactcc ctcccaccca ttaggccaac ctgctgccat   240
aggacccaag gtcaaaaagg aaagggcct gtttgtgtgg cgctggaggg ttagtcgtgt    300
gatctagacr tgaatgctca agtggcagga agcgtctgaa atcagagcta acttgggagg   360
cagaaaactc ggggttcccg gaagggagcc agagggtggt gcgaggctca cgccaggagg   420
ggaatgaaag cctgttctgt ggccacccag acccttccgt cagagctggc cacttctgcc   480 tttgaaagt gtttcacaat gccccgggca tgtgtgagga cagccaagtt gagctgaaga    540
tgcgtaaaag gctatagacc cacacactca ccggttccca gagaggacgg gtggaccaga   600
gagccaccca gcacaccact cacacagaga gcatctgagt ctgtggtcct catgacaggt   660
gagtagcccc ctctgtccag ggacagagcc tggattggag caggaggaga gcatcaggag   720
gggcaaggga agcccccrggt cccctgtggg agtcctggtc ttgaccacaa ttctggacag   780
gagcctgggg tcaggcgctt cacgttgcca agggcagagc ctcccccctgc ctcatctctg   840 tgggtttgga acctctgggg tttccctgga agctggaggc agggatgaga ccaaaggaca   900
cacacgttgg cgtcagtctt ccctgctcag agcc                              934

<210> SEQ ID NO 8
<211> LENGTH: 23
<212> TYPE: DNA
<213> ORGANISM: Sus scrofa

<400> SEQUENCE: 8
tgarcycttc atttaacaga aga                                           23

<210> SEQ ID NO 9
<211> LENGTH: 20
<212> TYPE: DNA
<213> ORGANISM: Sus scrofa

<400> SEQUENCE: 9
ggctctgagc agggaagact                                               20
```